United States Patent [19]

Avery et al.

[11] Patent Number: 5,411,585
[45] Date of Patent: May 2, 1995

[54] PRODUCTION OF STABLE HYDROLYZABLE ORGANOSILANE SOLUTIONS

[75] Inventors: Richard W. Avery; Frederick H. Martin; Sean G. Dwyer, all of Racine County, Wis.; Colin W. Brown, Middlesex County, England

[73] Assignee: S. C. Johnson & Son, Inc., Racine, Wis.

[21] Appl. No.: 269,949

[22] Filed: Jun. 30, 1994

Related U.S. Application Data

[63] Continuation of Ser. No. 98,331, Jul. 30, 1993, abandoned, which is a continuation-in-part of Ser. No. 657,017, Feb. 15, 1991, abandoned.

[51] Int. Cl.⁶ ............................................. C08K 5/54
[52] U.S. Cl. ........................... 106/287.1; 106/287.11; 106/287.12; 106/287.13; 106/287.14; 106/287.15
[58] Field of Search ........... 106/287.1, 287.11, 287.12, 106/287.13, 287.14, 287.15

[56] References Cited

U.S. PATENT DOCUMENTS

| | | | |
|---|---|---|---|
| 3,716,569 | 2/1973 | Redmore et al. | 260/448.8 N |
| 4,005,025 | 1/1977 | Kinstedt | 252/89 R |
| 4,005,118 | 1/1977 | Heckert et al. | 260/448.8 R |
| 4,005,119 | 1/1977 | Heckert et al. | 260/448.8 R |
| 4,259,103 | 3/1981 | Malek et al. | 71/67 |
| 4,395,454 | 7/1983 | Baldwin | 428/290 |
| 4,576,728 | 3/1986 | Stoddart | 252/102 |
| 4,597,964 | 1/1986 | Ziemelis et al. | 424/70 |
| 4,682,992 | 7/1987 | Fuchs | 55/279 |
| 4,845,256 | 7/1989 | Mebes et al. | 556/413 |
| 5,073,195 | 12/1991 | Cuthbert et al. | 106/2 |

FOREIGN PATENT DOCUMENTS

| | | | |
|---|---|---|---|
| 63-230170 | 9/1988 | Japan | A61L 9/01 |
| 01-260065 | 10/1989 | Japan . | |
| 01-266278 | 10/1989 | Japan . | |
| 1386876 | 3/1975 | United Kingdom | A01N 9/20 |

OTHER PUBLICATIONS

Chemical Abstract No. 103:106261w, Japanese Kokai JP 60–48,908 to Sanyo Chemical Industries Mar. 1985.

*Primary Examiner*—David Brunsman
*Attorney, Agent, or Firm*—R. E. Rakoczy; J. W. Frank

[57] ABSTRACT

A method of improving the stability and broadening the range of pH stability of an aqueous solution of from about 0.001% to 5% by weight of a water soluble organosilane containing hydrolyzable groups such as methyltrimethoxysilane, 3-(trimethoxysilyl)propyldimethyloctadecyl ammonium chloride and 3-(trimethoxysilyl)propylmethyldi(decyl) ammonium chloride by the use of 0.05% to 10% by weight of a water soluble organic quaternary ammonium compound having at least one nitrogen-bonded hydrocarbon group of at least 8 carbon atoms and being free of silicon atoms, such as benzalkonium chloride, along with from about 0.5% to 30% by weight of at least one surfactant selected from the group consisting of nonionic, amphoteric sarcosine anionic, and cationic surfactants other than the water soluble quaternary ammonium compounds. The pH of the solution can be adjusted to from about 1 to about 13.5 with a suitable acid or base. The resulting stable aqueous solutions are useful for depositing the water soluble organosilane on a variety of substrates to, among other things, serve as coupling agents, waterproofing agents and to render substrates antimicrobial and algicidal depending upon the nature of the organosilane.

52 Claims, No Drawings

PRODUCTION OF STABLE HYDROLYZABLE ORGANOSILANE SOLUTIONS

This is a continuation of application Ser. No. 08/098,331, filed on Jul. 30, 1993, now abandoned, which is a continuation-in-part of U.S. Ser. No. 07/657,017, filed on Feb. 15, 1991, now abandoned.

TECHNICAL FIELD

This invention relates to a method of improving the stability and broadening the range of pH stability of an aqueous solution of a water soluble organosilane containing silicon-bonded hydrolyzable groups, particularly water soluble quaternary ammonium functional organosilanes, by the addition of a water soluble organic non-silicon quaternary ammonium compound and at least one of nonionic, amphoteric, sarcosine anionic, and certain types of cationic surfactants as well as to the stabilized solutions themselves.

BACKGROUND ART

Water soluble organosilanes containing silicon-bonded hydrolyzable groups such as alkoxysilanes have a number of uses. The hydrolyzable groups enable such compounds to permanently attach themselves to substrates containing hydroxyl or other silicon-reactive groups. These organosilanes can be used in waterproofing cement, brick and mortar as well as to provide a further reactive group bonded to various substrates to enable that substrate to be dyed or painted or else to render the substrate antimicrobial or algicidal, among other things, depending upon the nature of the remaining silicon-bonded reactive groups which are not hydrolyzable.

For ecological reasons, it is more desirable to deliver such organosilanes to a substrate from a substantially aqueous medium which contains as few solvents as possible. Organosilanes are often used as coupling agents to improve the bonding of fillers to resins such as the unsaturated polyester resins used to make fiberglass boats, shower stalls and the like and can be applied from aqueous solutions. Page 58 of a brochure from Petrarch Systems of Bristol, Pa., entitled "Silicon Compounds, Register & Review", 1987, states that the stability of aqueous silane solutions varies from hours for the simple alkyl silanes to weeks for the aminosilanes. It states that the alkoxysilane is dissolved at 0.5–2.0% concentration in water. For less soluble silanes, 0.1% of a nonionic surfactant is added just prior to addition of the silane so that an emulsion rather than a solution is formed.

Further comments on the instability in water of organosilanes containing hydrolyzable groups are found in "A Guide to Dow Corning Silane Coupling Agents", Dow Corning Corporation, Midland, Mich., Form No. 23-012B-85 (1985) on pages 6–7 teaching that self-condensation of the silanol form of the organosilane coupling agent to form siloxane polymers is an important side reaction, particularly in aqueous pretreatment solutions and at a pH greater than 7. It teaches that with organosilanes that form water soluble polymers such as aminosilanes, the solution remains effective as a pretreatment. In the case of nonpolar silanes such as methyltrimethoxysilane and 3-chloropropyltrimethoxysilane, it teaches that precipitation can occur on long standing and coupling activity lost. The brochure states that, in such cases, it is especially important to use fresh solutions and to avoid high pH ranges which promote organosilane condensation. Page 11 of a newer version of this brochure published in 1990 as Brochure No. BL40531 teaches that dilute aqueous solutions of silane coupling agents should be prepared fresh daily.

On pages 94–95 of "Research Chemicals Catalog, Chemicals for Research Scientists", from PCR, Inc. of Gainesville, Fla. (1988), an aqueous solution of organosilanes is taught using 0.5–2% organosilane and 99.5–98.0% water along with sufficient acetic acid to obtain a solution a pH of 3.5–5.0 with pH 3.5 being preferred. The acetic acid is said to be unnecessary for aminosilanes. Additionally, 0.1% of nonionic wetting agents can be added to improve the solubility of the organosilanes and wet-out performance. Page 94 states that solution instability is determined by a change from clear solution to hazy. It states that most hydrolyzed organosilanes go through a condensation reaction to form products which are insoluble in aqueous solutions and, at that point, the solution should no longer be used.

Quaternary ammonium functional organosilanes containing hydrolyzable groups such as those sold under the trademark DOW CORNING® 5772 (3-(trimethoxysilyl)propyldimethyloctadecyl ammonium chloride) by Dow Corning Corporation of Midland, Mich. and REQUAT® 1977 (3-(trimethoxysilyl)propylmethyldi(decyl) ammonium chloride) by Sanitized, Inc. of New Preston, Conn. have found a large number of uses because of their ability to attach themselves to a wide variety of substrates where the quaternary ammonium functional group then acts as an antimicrobial and algicidal agent. Substrates treated with such quaternized organosilanes have also been noted to, among other things, be easier to clean, possess soil release properties, and cause hair to exhibit a conditioned appearance.

A very attractive medium from which such quaternized organosilanes can be applied is from an aqueous medium as is taught in U.S. Pat. No. 3,817,739 to Abbott et al., but the silicon-bonded hydrolyzable groups present in such quaternized organosilanes tend to cause them to be unstable due to hydrolysis and subsequent polymerization of the quaternized organosilane when there is more than one such hydrolyzable group per molecule. Abbott et al. tested aqueous solutions of 3-(trimethoxysilyl)propyldimethyloctadecyl ammonium chloride at 3 different pH values (3.8, 7.1 and 9.0) to determine if the pH of the solution affected the durability or effectiveness of the resulting organosilane coating. While they found that neutral to alkaline pH values were preferred for algae control effectiveness, there is no comment on the stability of the aqueous solutions of the quaternized organosilane. U.S. Pat. No. 3,730,701 to Isquith et al. describes a method of controlling algae in aqueous media using quaternized organosilanes and U.S. Pat. No. 3,794,736 to Abbott et al. describes the use of certain organosilylamines containing hydrolyzable groups and their salts for inhibiting the growth of bacteria and fungi.

Quaternized organosilanes are often applied from solvent solutions such as lower alcohols and the commercial versions of these quaternized organosilanes are commonly provided as methanolic solutions.

Another alternative is to form a clear microemulsion of a quaternized organosilane using a cosurfactant having an HLB value of at least 1 as is taught in U.S. Pat. No. 4,842,766 to Blehm et al. However, this patent teaches that the methanol-based solvent in which the organosilane is supplied must be removed before blending the quaternized organosilane with the cosurfactant (e.g., a nonionic surfactant can used). If the methanol is not removed, a creamy white emulsion forms which is unstable and will separate into oil and water phases over time. The '766 Patent also teaches that high shear may have to be applied to the mixtures of organosilane and cosurfactant to ensure codispersion. Obviously, this has the disadvantage of requiring a homogenization step to prepare such microemulsions. Blehm et al. teach that almost any surfactant can be employed including anionic, cationic, amphoteric or zwitterionic surfactants as well as nonionic surfactants although nonionic surfactants and compounds such as glycerol, ethylene glycol, propylene glycol and higher monoalcohols such as pentanol, decanol and decanediol are most preferred.

Another patent teaching oil-in-water emulsions containing 3-(trimethoxysilyl)propyldimethyloctadecyl ammonium chloride as well as, optionally, cosurfactants such as nonionic and cationic surfactants, is U.S. Pat. No. 4,631,273 to Blehm et al. These emulsions employ a homogenizer using high shear conditions and teach that the quaternized organosilane does not hydrolyze while it is in emulsion form and thus does not polymerize to an insoluble siloxane. The Examples use ARQUAD® T27W cationic surfactant which is trimethyl tallow ammonium chloride. However, these emulsions also require a water immiscible liquid such as a polydimethylsiloxane or a mineral oil with which the quaternized organosilane associates. Blehm et al. teach that a sufficient shear force is necessary to form the emulsions they teach and that an Eppenbach mixer did not provide a sufficient amount of such shear.

U.S. Pat. No. 4,847,088 to Blank teaches that the combination of a quaternized organosilane such as 3-(trimethoxysilyl)propyldimethyloctadecyl ammonium chloride with an acid such as citric acid or boric acid in water results in a composition which exhibits synergistic antimicrobial effects. In Table I, Sample III contained water, 3-(trimethoxysilyl)propyldimethyloctadecyl ammonium chloride and ARQUAD® T2 quaternary ammonium cationic surfactant as a comparative example. According to the manufacturer, ARQUAD® T2 is a mixture of dicocodimethyl ammonium chloride and trimethyltallow ammonium chloride. Nothing is taught about the pH or the stability of this composition and the patent teaches away from the use of Sample III in favor of compositions containing the acid, the quaternized organosilane and water only, even though the cationic ARQUAD® T2 surfactant was said to possess antimicrobial properties. Examples 43–46, below, describe the results of an experiment using the same ingredients as were used in Sample III, Table I, of the Blank '088 Patent. The solutions were found to be stable after 4.5 weeks of both room temperature storage and accelerated aging storage at 60° C. However, the Blank '088 Patent does not suggest that ARQUAD® T2 should act as a stabilizer for aqueous silane solutions nor does it suggest that the combination of two different types of surfactants is necessary to achieve such storage stability nor does it suggest that such an additive would broaden the pH stability of such solutions.

PCT International Publication No. WO 87/00006 to Schafer teaches a plant microbiocidal compound for plants in the form of an aqueous solution of 3-(trimethoxysilyl)propyldimethyloctadecyl ammonium chloride which can further include a nonionic surfactant and wetting agent such as polyoxyethylene ethers such as TRITON® X-100 from Sigma Chemical Co. of St. Louis, Mo. or polyoxyethylenesorbitan monooleate such as TWEEN® 80 from Sigma Chemical Co. Nothing is taught concerning the stability or the pH of the solutions.

U.S. Pat. No. 4,564,456 to Homan teaches a method of treating water to inhibit corrosion and diminish mineral deposition as well as in industrial and household cleaning compositions through the use of cationic organosilanes such as 3-(trimethoxysilyl)propyldimethyloctadecyl ammonium chloride in an aqueous medium where the pH of the medium is neutral or alkaline. The cationic organosilane is intended to stay in the aqueous medium such as a home humidifier reservoir or water cooling system for an extended period of time.

U.S. Pat. No. 4,567,039 to Stadnick et al. teach a hair conditioning composition which uses an organosilane such as 3-(trimethoxysilyl)propyldimethyloctadecyl ammonium chloride as the hair conditioning agent in an aqueous/organic solvent which can further contain nonionic surfactants as solubilizers. A base is used to adjust the pH of the composition to the required alkaline range of from 8 to 10 to cause swelling of the hair. Stadnick et al. teach that when a base is added to adjust the pH to the desired range, the organosilane tends to polymerize and precipitate. Stadnick et al. therefore caution that the composition should be prepared just before use on the hair or packaged as a two part system to avoid this instability problem.

U.S. Pat. No. 4,421,796 to Burril et al. teaches a method of treating textile fibers with an emulsion composition containing a polydimethylsiloxane and a quaternary ammonium functional organosilane to obtain textiles with improved removal of oily soil as well as with antistatic properties.

Canadian Pat. No. 1,217,004 to Hardy teaches an aqueous hypochlorite bleach composition of pH 10 to 12 which is free of anionic surfactants and further contains a $C_{16}$ to $C_{20}$ alkyl quaternized organosilane such as 3-(trimethoxysilyl)propyldimethyloctadecyl ammonium chloride as a bactericidal additive which renders the surface of a siliceous substrate treated with such a composition antibacterial and easier to clean. The compositions can further contain thickening agents as well as amine oxide or betaine surfactants. Hardy teaches that quaternized organosilanes having alkyl groups with less than 16 carbon atoms tend to be too water soluble and display markedly impaired surface substantivity when used in the presence of hypochlorite stable surfactants. The stability of the quaternized organosilanes in these strongly alkaline compositions is also discussed.

The following patents deal with the inclusion of organosilanes such as 3-(trimethoxysilyl)propyldimethyloctadecyl ammonium chloride in detergent compositions: U.S. Pat. Nos. 4,005,025 to Kinstedt, 4,005,028 to Heckert et al. and 4,005,030 to Heckert et al.

The '025 Patent teaches that the detergent compositions containing anionic surfactants and quaternized organosilanes can be used for cleaning metallic and vitreous surfaces such as toilet bowls and leave behind a soil-releasing coating. It teaches that little or no enhancement of deposition of the quaternized organosilane occurs below a solution pH of 8.5 with a steep rise in deposition over the pH range of 8.5–10.0 and a smaller increase in deposition occurs above pH 10.0. The patent also teaches that aqueous products which have phase instability after 1 day at neutral pH (6.5–7.5) are stable for indefinite periods at higher pH values (pH 10-12). Nonionic surfactants can optionally be included.

The '028 Patent is similar to the '025 Patent, but the detergent composition employs nonionic, zwitterionic or ampholytic detergents along with the quaternized organosilane and prefers the use of nonionic surfactants. Little is said concerning stability and pH.

The '030 Patent is similar to the '025 Patent and consists essentially of a detergent composition containing an anionic surfactant and a quaternized organosilane such as 3-(trimethoxysilyl)propyldimethyloctadecyl ammonium chloride with no restriction on the pH of the compositions.

U.S. Pat. No. 4,797,420 to Bryant teaches a disinfectant formulation based on an alkyl dimethylbenzyl ammonium chloride in water along with a nonionic surfactant and a lower alcohol such as isopropanol. Bryant teaches nothing concerning the further inclusion of water soluble organosilanes into his compositions.

U.S. Pat. No. 4,517,375 to Schmidt teaches aqueous impregnating solutions prepared from hydrolyzed alkyltrialkoxysilanes where the alkyl group can contain from 1 to 4 carbon atoms. The solutions are said to be stable and remain free of turbidity for as long as 80 hours when prepared at room temperature and the pH of the solution is between 1 and 7, preferably between a pH of 2 to 3.5, using a mineral acid or an organic acid to adjust the pH. Aqueous solutions of the present invention are stable for significantly longer periods of time and over a broader range of pH values.

U.S. Pat. No. 4,648,904 to DePasquale et al. teaches aqueous systems containing silanes containing 2 or 3 hydrolyzable groups such as halide or $C_1$-$C_3$ alkoxy groups and one or two hydrocarbyl groups containing from 1 to 20 carbon atoms and an emulsifying agent having an HLB value of from 4 to 15 along with water. DePasquale et al. generally teaches that all types of emulsifying agents can be used, including cationic surfactants, but teaches away from their use to prefer nonionic surfactants which are preferably polyhydroxy materials. DePasquale et al. also teach that the surfactants, particularly the polyhydroxy type such as the SPAN ® sorbitan fatty acid esters and TWEEN ® polyethylene sorbitan fatty acid esters, are hydrolysis inhibitors in the absence of an acid or alkaline medium. In the acid or alkaline medium of masonry such as concrete, the silanes are said to hydrolyze and thus deposit on that substrate. Thus, DePasquale appears to favor a neutral pH medium while the present invention permits the formation of stable aqueous solutions across a wide range of pH values.

SUMMARY OF THE INVENTION

What the prior art has failed to recognize is that certain organosilanes containing hydrolyzable groups, especially quaternary ammonium functional organosilanes, can form clear solutions in aqueous media which are stable over extended periods of time without the use of emulsion technology involving the application of high shear forces by further including a water soluble organic, non-silicon quaternary ammonium compound along with nonionic, amphoteric, sarcosine anionic or certain cationic surfactants. These compositions can be made simply by adding the ingredients together and adjusting the pH across a wide range of pH's, for example, from about pH 1 to about 13.5, without having to maintain the solution within specific pH ranges to maintain the stability of the organosilane as has been taught in the prior art. The method of the present invention provides stable, clear organosilane solutions which are capable of depositing the organosilane on a substrate after an extended period of time and are thus useful in forming compositions or treating substrates to render them, for example, hydrophobic, hydrophilic, reactive, or antimicrobial. These solutions are particularly advantageous for coupling agent application solutions, in household and industrial cleaning compositions where an antimicrobial and soil-releasing substrate is desired and for the many other uses which organosilanes can be used.

The organosilanes having hydrolyzable groups which are useful in this invention must be water soluble at room temperature (25° C.) at least to the extent of the active concentration level to be used in the aqueous solutions. Examples of such organosilanes are methyltrimethoxysilane, 3-(trimethoxysilyl)propyldimethyloctadecyl ammonium chloride and 3-(trimethoxysilyl)propylmethyldi(decyl)ammonium chloride. We have found that compounds which do not give clear solutions in water at 25° C., such as 3-(triethoxysilyl)propyldimethyloctadecyl ammonium chloride are not useful in the present invention. The organosilane is present in the aqueous solution in an amount of from about 0.001% to 5% by weight, more preferably from 0.01% to 2% by weight and most preferably from 0.05% to 0.5%.

Likewise, the organic quaternary ammonium compound must be water soluble at least to the extent of forming a clear solution in water at 25° C. at least to the extent of the active concentration to be used. It further must contain at least one nitrogen-bonded hydrocarbon group of at least eight carbon atoms and is free of silicon atoms. One example of a useful organic quaternary ammonium compound is benzalkonium chloride. The amount of water soluble organic quaternary ammonium compound is 0.05% to 10% by weight based on the total weight of the aqueous solution and more preferably is from 0.1% to 5% by weight and most preferably from 0.1% to 1.2% by weight.

The present invention also employs from about 0.5% to 30% by weight based on the total weight of the aqueous solution of nonionic, amphoteric, sarcosine anionic or cationic surfactant other than the foregoing cationic compounds with nonionic surfactants being preferred with the first three groups of surfactants being most preferred. Examples of such surfactants are polyethoxylated ethers of decyl alcohol containing 6 or 9 ethoxy groups per molecule, tetramethyl decynediol and an ethoxylated and propoxylated lauryl alcohol. The surfactants are present in an amount of from about 0.5% to 30% by weight and more preferably is present in an amount of from about 1 to 5% and most preferably, from about 1% to 2.2% by weight of the aqueous solution. Other than sarcosines, anionic surfactants should be avoided due to possible instability problems with the organic quaternary ammonium compound.

The pH of the aqueous solutions is adjusted with citric acid, hydrochloric acid, sodium carbonate, sodium hydroxide or other suitable acids and bases to a pH in the range of from about 1 to about 13.5.

Thus the method involves preparing an aqueous solution of the organosilane to which is added the cationic surfactant and the nonionic or other surfactant, optionally followed by or along with a suitable acid or base to obtain the desired pH.

BEST MODE FOR CARRYING OUT THE INVENTION

These and other advantages of the present invention are provided by a method of improving the storage stability and broadening the range of pH stability of an aqueous solution containing from about 0.001% to 5% by weight of a water soluble organosilane of the formula $$A_{3-x}B_xSiD$$

provided that the organosilane forms a clear solution in water at 25° C. at the intended level of use, which method comprises including within the solution
  a. from about 0.05% to 10% by weight of the total aqueous solution of a water soluble organic quaternary ammonium compound which is free of silicon atoms and contains at least one nitrogen-bonded hydrocarbon group of at least 8 carbons and
  b. from about 0.5% to 30% by weight of the total aqueous solution of at least one surfactant selected from the group consisting of nonionic, amphoteric, sarcosine anionic, and cationic surfactants other than the compounds of (a);
wherein the amounts of (a) and (b) present are effective to improve the storage stability of and to broaden the pH stability of the resulting solution and each
  A is —OH or a hydrolyzable group,
  B is an alkyl group of from 1 to 4 carbon atoms,
  x has a value of 0, 1 or 2, and
  D is a hydrocarbon group of from 1 to 4 carbon atoms, phenyl, or a nonionic or cationic, substituted-hydrocarbon group containing at least one oxygen or nitrogen group or salts of such substituted-hydrocarbon groups.

This invention further relates to a method of improving the storage stability and broadening the pH stability of an aqueous solution containing from about 0.001% to 5% by weight of a water soluble organosilane of the formula $$A_{3-x}B_xSiD$$

where A, B, x and D are as defined above and provided that the organosilane forms a clear solution in water at 25° C. at the intended level of use, which method comprises
  I. including within the solution
    a. from about 0.05% to 10% by weight of the total aqueous solution of a water soluble organic quaternary ammonium compound which is free of silicon atoms and contains at least one nitrogen-bonded hydrocarbon group of at least 8 carbons and
    b. from about 0.5% to 30% by weight of the total aqueous solution of at least one surfactant selected from the group consisting of nonionic, amphoteric, sarcosine anionic, and cationic surfactants other than the compounds of (a); wherein the amounts of (a) and (b) present are effective to improve the storage stability of and to broaden the pH stability of the resulting solution; and
  II. including within the solution a sufficient amount of an acid or a base to obtain a solution pH of from about 1 to 13.5.

The aqueous solutions produced by the present invention employ water as the carrier medium. Preferably, the water is distilled or deionized to remove minerals and other contaminants. Optionally, from about 0.1 to 25% by weight of the total aqueous solution can be water soluble solvents such as butyl carbitol, dipropylene glycol monomethylether, propylene glycol, carbitol, methoxypropanol, glycerine, isopropanol, ethanol and the like. Preferably, methanol is avoided although the methanol present in commercially available solutions of quaternary ammonium functional organosilanes is well tolerated by the aqueous solutions prepared by the method of the present invention.

Organosilanes useful in the present invention are well known compounds and a number of them are commercially available from General Electric Company of Waterford, N.Y., Union Carbide Corporation of Danbury, Conn. and Dow Corning Corporation. The Petrarch Systems *Silicon Compounds Register and Review* also lists a large variety of commercially available organosilanes offered by that company. Examples of aminosilanes and quaternary ammonium functional organosilanes can be found in U.S. Pat. Nos. 3,730,701 to Isquith et al.; 3,794,736 to Abbott et al.; 4,259,103 to Malek et al.; and 4,406,892 to Eudy, and Canadian Pat. No. 1,010,782 to Roth. Other patents describing methods of making such quaternized organosilanes are U.S. Pat. Nos. 4,282,366 to Eudy, 4,394,378 to Klein and 3,661,963 to Paep et al. Specific examples of structural formulas of such quaternized organosilanes can be seen in U.S. Pat. No. 4,847,088 to Blank.

As noted above, one requirement is that the organosilanes used in the present invention be "water soluble" at room temperature (25° C.) to be useful. We have found that if the organosilanes are not sufficiently water soluble to form a clear solution at room temperature at the levels at which the organosilanes are to be included in the aqueous solutions, then the method of the present invention does not produce clear and stable solutions. For example, we have found that 3-(triethoxysilyl)-propyldimethyloctadecyl ammonium chloride was not sufficiently water soluble to be useful in the present invention. 3-chloropropyltrimethoxysilane was found to be reactive in aqueous solution and was not stabilized in aqueous solution by this invention. This can be determined simply by dissolving the organosilane in distilled or deionized water at room temperature at the desired level of use and observing whether or not the organosilane initially forms a clear solution and is thus "water soluble" for the purposes of this invention in the attached Claims.

In the above formulas, A is —OH or a hydrolyzable group such as a halide like —Cl, —Br, and —I, alkoxy or alkoxyether such as those of the formula —OR$^1$ and —OR$^{2A}$OR$^1$ where each R$^1$ is R$^2$ or hydrogen, R$^2$ is an alkyl group of from 1 to 4 carbon atoms such as methyl, ethyl, propyl, butyl or —CH$_2$CH$_2$CH$_2$(CH$_3$), with methyl being preferred, and R$^{2A}$ is a divalent saturated hydrocarbon group of from 1 to 4 carbon atoms such as methylene, ethylene, propylene, butylene or —CH$_2$CH$_2$CH(CH$_3$)—with ethylene and propylene being preferred; amino such as —N(R$^1$)$_2$ such as —NHCH$_3$, —N(CH$_3$)$_2$, and —N(CH$_2$CH$_2$)$_2$, also including organosilazanes where two organosilanes are combined by a —NH—unit; acetoxy which is —OOCCH$_3$; acetamido which is —HNOCCH$_3$; and hydride which is —H, among others known in the art.

B is R$^2$ with methyl being preferred.

D is a hydrocarbon group such as R², vinyl, allyl, phenyl, and nonionic or cationic, substituted-hydrocarbon groups containing at least one oxygen or nitrogen group as well as salts of such substituted-hydrocarbon groups. Examples of the latter substituted-hydrocarbon groups include

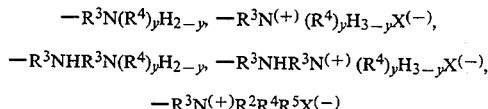

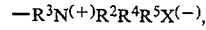

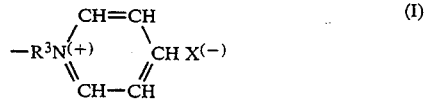

and —R³Q where Q represents a functional group, optionally with further alkyl or aryl chains, such as alcohols and ethers such as —(OCH₂CH₂)$_z$OR¹ where z has a value of from 0 to about 50, esters or amides such as —COOR⁶, —CONHR⁶, —HNOCR⁶ or —OOCCH(R⁶)$_x$H$_{1-t}$CHCH₂ where R⁶ is an alkyl group of 1 to 18 carbon atoms such as methyl, ethyl, butyl, octyl, and octadecyl with methyl being preferred and t is 0 or 1, glycidoxy such as —OCH₂CHOCH₂ as well as other nonionic or cationic substituted-hydrocarbon groups known in the art. In the above formulas, x has a value of 0, 1 or 2 with values of 0 or 1 being preferred, and with x having a value of 0 being most preferred; y has a value of 0, 1 or 2; R³ is a divalent saturated hydrocarbon group of from 1 to 12 carbon atoms such as R²$^4$, —(CH₂)₆—, —(CH₂)₈—, and —(CH₂)₁₂—; R⁴ and R⁵ are each selected from the group consisting of alkyl groups of 1 to 18 carbon atoms, —CH₂C₆H₅, —CH₂C-H₂OH and —CH₂OH. R⁶ is an alkyl group of 1 to 18 carbon atoms. One example of —R³Q is glycidoxypropyl or —(CH₂)₃OCH₂CHOCH₂. X is an anion and, more preferably, is selected from chloride, bromide, fluoride, iodide, acetate, methosulfate, ethosulfate, phosphate or tosylate anions, and most preferably, X is a chloride anion.

In Formula (I) above, R⁴ and R⁵ are preferably alkyl groups of from 1 to 18 carbon atoms and more preferably, R² is a methyl group with the total number of carbon atoms in R³, R⁴ and R⁵ being at least 12 if antimicrobial properties are desired from the organosilane. In one preferred organosilane of Formula (I), R³ is a propylene, R² and R⁴ are each methyl groups and R⁵ is an octadecyl group while in another alternative preferred organosilane of Formula (I), R² is a methyl group and R⁴ and R⁵ are each decyl groups.

The most preferred compounds for use in the present invention are (CH₃O)₃SiR², particularly where R² is methyl, (CH₃O)₃SiCH=CH₂, (CH₃O)₃SiCH₂CH=CH₂, (CH₃O)₃SiCH₂CH₂CH₂OCH₂CHOCH₂, (CH₃O)₃SiR²N(R⁴)$_y$H$_{2-y}$, (CH₃O)₃SiR³N(+)(R⁴)$_y$H$_{3-y}$X(−), (CH₃O)₃SiR³NHR³N (R⁴)$_y$H$_{2-y}$, (CH₃O)₃SiR³NHR³N(+)(R⁴)$_y$H$_{3-y}$X(−),

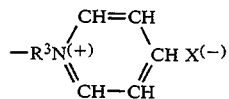

where R³ is propylene and, of the nitrogen-functional organosilanes, the most preferred are 3-(trimethoxysilyl)propyldimethyloctadecyl ammonium chloride having the formula

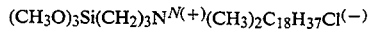

and 3-(trimethoxysilyl)propylmethyldi(decyl)ammonium chloride which has the formula

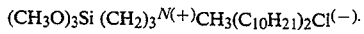

One requirement of the present invention is the presence of from about 0.05% to 10% by weight of the total aqueous solution of a water soluble organic quaternary ammonium compound which is free of silicon atoms and contains at least one nitrogen-bonded hydrocarbon group of at least 8 carbon atoms. It is not understood why the presence of such an organic quaternary ammonium Compound assists in stabilizing the water soluble organosilanes used in the present invention. Water insoluble quaternary ammonium compounds do not assist in stabilizing the organosilanes used in the present invention. The same room temperature (25° C.) water solubility test is used for these compounds as was described above for the organosilanes. Such quaternary ammonium compounds include salts such as isostearyl benzyldimonium chloride, isononamidopropyl ethyldimonium ethosulfate, lapyrium chloride, steapyrium chloride, stearamidopropalkonium chloride, stearyl hydroxyethyldimonium chloride, and those of the formulas R⁷R⁸N(+)(R²)₂X(−) and C₅H₅N(+)R⁷X(−) wherein R⁷ is selected from the group consisting of alkyl groups of from about 6 to 18 carbon atoms, and R⁸ is selected from the group consisting of R² and —CH₂C₆H₅ as well as the corresponding quaternary ammonium hydroxide compounds such as benzyltrimethylammonium hydroxide. The salts are more preferred since they do not add unnecessary alkalinity to the solutions.

Specific examples of such quaternary ammonium compounds are benzalkonium chloride which is a mixture of alkylbenzyldimethylammonium chlorides of the formula C₆H₅CH₂N(+)R⁷(CH₃)₂Ci(−) where R⁷ is a mixture of alkyl groups beginning with capryl (C₆) and extending through higher homologs with lauryl (C₁₂), myristyl (C₁₄), and cetyl (C₁₆) predominating, lauralkonium bromide, lauralkonium chloride, stearalkonium chloride, laurtrimonium chloride, cocotrimonium chloride, myrtrimonium bromide, didecyldimonium chloride, cetylethyldimonium bromide, cetrimonium chloride, cetrimonium bromide, cetrimonium tosylate, isostearyl ethyldimonium chloride, isostearyl ethyldimonium ethosulfate, steartrimonium chloride, laurylpyridinium chloride, myristalkonium chloride, cetylpyridinium chloride, and stearylpyridinium chloride. It appears that quaternary ammonium compounds which have anti-microbial properties are typically useful as quaternary ammonium surfactants in the present invention. Benzalkonium chloride is presently preferred.

A further required ingredient is from about 0.5% to about 30% of at least one surfactant which can be a nonionic, amphoteric, sarcosine anionic or cationic surfactant other than the quaternary ammonium compounds noted above. The first three classes of surfactants are most preferred. The term "amphoteric" surfactant includes "zwitterionic" surfactants for the purposes of this invention since those terms are often used almost interchangeably. It also appears that surfactants which are more hydrophilic, for example, by virtue of longer chain ethoxy groups, serve to better stabilize the aqueous solutions of silanes using smaller amounts of such surfactants for a given amount of silane than those which are less hydrophilic and thus more hydrophobic in character as shown in some of the Examples below.

These surfactants are well known and a large number are commercially available as can be seen from an examination of "McCutcheon's Emulsifiers & Detergents", either the North American Edition or the International Edition, for 1989 and 1990 published by the McCutcheon Division, MC Publishing Co. of Glen Rock, N.J. as well as in the "CTFA Cosmetic Ingredient Dictionary", Third Edition, Estrin et al., Editors, 1983 and the 1985 Supplement thereto by The Cosmetic, Toiletry and Fragrance Association, Inc. of Washington, D.C. More preferably, the surfactant is used in an amount of 0.1% to 5% by weight of the total aqueous solution with from 1% to about 2.2% being typical unless the aqueous solution is being used in a detergent formulation where higher amounts of surfactant are needed.

Examples of nonionic surfactants include $C_8$ to $C_{18}$ alcohol ethoxylates containing from about 3 to 50 moles of ethylene oxide such as ethoxylated $C_{10}$ alcohols averaging 6, 7 or 9 moles of ethylene oxide per molecule, an ethoxylated saturated fatty alcohol containing an average of 50 moles of ethylene oxide per molecule sold under the tradename "GENAPOL ® T5OOP" by Hoechst AG of Frankfurt, West Germany, an ethoxylated $C_{13}$–$C_{15}$ alcohol containing 8 moles of ethylene oxide per molecule as well as other surfactants having up to 30 moles of ethylene oxide per molecule sold under the tradename "LUTENSOL ® AO" by BASF AG of Ludwigshafen, West Germany and polyethoxylated oleyl, lauryl, cetyl and stearyl alcohols sold under the tradename "BRIJ ®" by ICI Americas, Inc. of Wilmington, Del.; $C_8$ to $C_{18}$ fatty acid esters of sorbitan or polyethoxylated sorbitan such as the laurate, oleate, stearate, and palmitate esters of sorbitan and sorbitan anhydride containing 0 or from about 4 to 20 moles of ethylene oxide sold under the tradename "SPAN ®" or "TWEEN ®" by ICI Americas; $C_8$ to $C_{18}$ fatty acid esters and amides containing from about 2 to 50 moles of ethylene oxide such as PEG-5 cocoate, PEG-15 cocoate, PEG-4 dilaurate, PEG-32 dilaurate, PEG-3 cocamide, PEG-6 cocamide, PEG-11 cocamide, PEG-20 dioleate, PEG-6 isopalmitate, PEG-12 isostearate, PEG-3 lauramide, PEG-8 laurate, PEG-32 laurate, PEG-4 octanoate, PEG-7 oleamide, PEG-2 oleate, PEG-14 oleate, PEG-20 palmitate, PEG-14 stearate, and PEG-5 tallowamide; $C_8$ to $C_{18}$ fatty alcohols such as caprylic alcohol, lauryl alcohol, cetyl alcohol and stearyl alcohol; $C_8$ to $C_{18}$ diols such as tetramethyl decynediol and dimethyl octynediol, block copolymers of polyethylene oxide and polypropylene oxide such as those containing from about 10 to 300 total units of ethylene oxide and propylene oxide sold under the tradename "PLURONIC ®" by BASF Corporation, Chemical Division, of Parsippany, N.J. and are listed as "Poloxamers" in the "CTFA Cosmetic Ingredient Dictionary"; and $C_8$ to $C_{18}$ fatty acid esters of glycerine such as glyceryl caprate, glyceryl isostearate, glyceryl laurate, glyceryl myristate and glyceryl oleate; ethoxylated and propoxylated $C_8$ to $C_{18}$ fatty alcohols such as ethoxylated and propoxylated lauryl alcohol sold under the tradename "DEHYPON ® LS" by Henkel KGaA of Dusseldorf, West Germany; and $C_8$ to $C_{18}$ fatty amine and amidoamine oxides such asodecylamine oxide, cocamine oxide, cocamidopropylamine oxide, myristamine oxide, myristamidopropylamine oxide, palmitamine oxide, and stearamine oxide; and $C_8$ to $C_{18}$ fatty amides and. alkanolamides such as cocamide, cocamide DEA, cocamide MEA, stearamide, stearamide DEA, stearamide MEA and stearamide MIPA. More preferred presently are the $C_8$ to $C_{18}$ fatty alcohol ethoxylates, tetramethyl decynediol, and ethoxylated and propoxylated lauryl alcohol.

Examples of amphoteric surfactants include $C_8$ to $C_{18}$ sultaines such as coco-sultaine and cocamidopropyl hydroxysultaine, $C_8$ to $C_{18}$ fatty derivatives of amino acids such as cocamphocarboxyglycinate and lauramphoglycinate, as well as the more preferred $C_8$ to $C_{18}$ alkyl betaines such as decyl betaine, coco-betaine, lauryl betaine, myristyl betaine and stearyl betaine; and $C_8$ to $C_{18}$ amidoalkyl betaines such as cocoamidoethyl betaine, cocamidopropyl betaine, lauramidopropyl betaine, myristamidopropyl betaine and oleamidopropyl betaine, stearamidopropyl betaine with the betaines being presently preferred.

Since sarcosine surfactants are known to be compatible with quaternary ammonium compounds, this class of anionic surfactants can be used in the present invention. Examples of such surfactants are $C_8$ to $C_{18}$ alkyl sarcosines and their alkali metal or ammonium salts such as sodium, potassium, lithium or ammonium $C_8$ to $C_{18}$ alkyl sarcosinates which include cocoyl sarcosine, lauroyl sarcosine, sodium lauroyl sarcosinate, potassium lauroy sarcosinate, lithium lauroyl sarcosinate, ammonium lauroyl sarcosinate, sodium cocoyl sarcosinate and potassium cocoyl sarcosinate with sodium lauroyl sarcosinate being presently preferred. If the $C_8$ to $C_{18}$ alkyl sarcosine is to be used, at least some of the acidic carboxyl groups should be neutralized with, for example, sodium hydroxide, to render the surfactant water dispersible.

Examples of cationic surfactants other than the quaternary ammonium compounds already described above are non-water soluble quaternary ammonium compounds which contain at least two nitrogen-bonded alkyl chains having at least about 16 carbon atoms such as distearyldimonium chloride and ditallowdimonium chloride and $C_8$ to $C_{18}$ fatty alkyl amines, amidoalkylamines and amidoalkanolamines, and their salts such as cocamine and cocamine hydrochloride, stearamine and stearamine hydrochloride, stearamidopropyl dimethylamine, stearamidoethyl diethylamine, and stearamidoethyl diethanolamine.

The pH of the aqueous solutions can be adjusted in the range of from about 1 to about 13.5 using an appropriate organic or inorganic acid such as citric acid, acetic acid, hydrochloric acid, phosphoric acid, sorbic acid or an organic or inorganic base such as ammonium hydroxide, sodium hydroxide, potassium hydroxide, ethyl amine, dimethyl amine, triethyl amine, ethanol amine, diethanol amine and triethanol amine. The advantage of the method of the present invention is that the aqueous solutions of the water soluble organosilanes are stable under a much wider range-of pH than is presently known in the art as will be shown in the Examples below. For example, the "Research Chemicals Catalog" brochure noted above teaches that aqueous solutions of alkyl silanes are brought to a pH of 3.5 to 5.0 using acetic acid, preferably to pH 3.5, but the solutions are said to form insoluble products which render the solutions hazy at which time the solutions should be discarded. Aqueous solutions made according to the present invention have a much longer period of useful life.

This is particularly true when the pH of the aqueous solution of water soluble silane is in the alkaline range of from about 8 to 10 where the literature teaches that condensation reactions leading to polymerization of the organosilane and solution instability are generally accelerated. Likewise, condensation of the organosilane is also accelerated at low pH values such as from 1 to 3. The preferred pH values for the present invention range from about 3 to 9 although for highly alkaline detergent formulations, a pH of from about 10 to 13 is used.

Optionally, other ingredients which are compatible with the water soluble organosilanes and surfactants may be included such as from about 0.1% to 5% based upon the total weight of aqueous solution of a thickening agent such as hydroxyethyl cellulose, xanthan gum, or conventional thickening agent. Particulate additives such as silica and other high surface area particles are to be avoided since the organosilane may deposit on such particles and thus remove it from the aqueous solutions. Similarly conventional additives such as perfumes, dyes, buffering agents, water soluble metal salts, detergent builders, chelating agents such as EDTA and salts thereof, and the like can be included in the aqueous solutions of the present invention provided that they are compatible with the other ingredients present.

INDUSTRIAL APPLICABILITY

The method of the present invention is carried out in a rather simple fashion in contrast to the more complex methods of stabilizing aqueous solutions of organosilanes via the formation of emulsions and the like. The water soluble organic quaternary ammonium compound is mixed with water with moderate stirring along with the nonionic, amphoteric, sarcosine anionic or other cationic surfactant, preferably at room temperature (about 25° C.), to form an aqueous solution. The water soluble organosilane, optionally dissolved in a small amount of the water to be included in the total solution, is simply dissolved in the resulting solution containing the surfactants with moderate stirring. The resulting solution is thus stabilized against the effects of changes in pH over a wide range compared with aqueous organosilane solutions not so stabilized.

If desired, the pH of the solution can be adjusted to the desired pH of from about 1 to about 13.5 using an appropriate acid or base. Adjustment of the pH does not have to be made subsequent to the formation of the stabilized solution, but can be done during the process of preparing the solution by inclusion of an appropriate amount of an acid or a base. Exposure of the organosilane alone in water to an acid or a base is preferably avoided at least until the stabilizing ingredients are added or are added simultaneously with the acid or the base. No high shear mixing or homogenization appears to be necessary and a visually clear aqueous solution results.. The aqueous solutions of 3-(trimethoxysilyl)-propyldimethyloctadecyl ammonium chloride and 3-(trimethoxysily)propylmethyldi(decyl)ammonium chloride) have been observed to remain stable at room temperature for weeks and have long storage times even when sealed samples are stored in an oven at 40° C. or 60° C. as is shown in the Examples. Solution instability can be evidenced by an increase in turbidity or by an increase in viscosity. Failure to produce a substrate adequately treated with the organosilane after contact with the aqueous organosilane solution is another indication of storage stability failure.

The method can be modified depending upon the end product to be prepared such as where a bathroom cleaning composition is to be made in which case an aqueous solution containing the organic quaternary ammonium compound, at least one surfactant and a thickening agent are prepared first, optionally with a first pH adjustment, followed by the addition of the water soluble organosilane and final pH adjustment. The water soluble organosilane can also be dissolved in water first and the surfactants added to that solution followed by pH adjustment. If the water soluble organosilane is first dissolved in water, the solution should be quickly used to avoid problems with instability. The order of addition can be changed as long as the solution storage stability is not significantly affected.

Aqueous solutions prepared according to the present invention can be used as surface treatment agents such as for coupling agent use to improve the substrate's acceptance of dyes, paint and floor treatments, as waterproofing agents when alkyl trimethoxysilanes are used, in cleaning compositions for bathrooms, kitchens, swimming pools, tiles, food areas and the like, particularly when organosilanes such as 3-(trimethoxysilyl)-propyl-dimethyloctadecyl ammonium chloride and 3-(trimethoxysily)-propylmethyldi(decyl) ammonium chloride are used which render the substrate being cleaned antimicrobial and algicidal, and for a wide variety of other uses for which water soluble organosilanes are known to be useful.

In the following Examples, certain tests were used:

Residual Antimicrobial Mold Test: In this test, 4 inch×4 inch (10.2 cm×10.2 cm) pieces of front glazed ceramic tile were divided into 2 cm×3 cm tiles.

In the "Standard Protocol" one drop (75 microliters) of the solution to be tested was placed in the center of the unglazed back side of the tile and allowed to dry for one hour at room temperature (25° C.). A second drop (75 microliters) of the same test solution was again placed on the previously treated area and allowed to dry for 3 more hours at 25° C. The tile was then rinsed with running tap water for 1.5 hours, dried overnight at room temperature, and was then exposed to a mold culture by adding and evenly spreading 0.075 ml of a mold culture which was a mixture of fungus spores to one half of the tile to be tested. The tile was allowed to dry and a second 0.075 ml aliquot of the mold culture was added to the same area. The other half of the tile to be tested was not contacted with the mold mixture. After the tiles were allowed to dry a second time, they were placed in a plastic box over a saturated solution of aqueous sodium phosphate. The air above the solution achieved 95% relative humidity. The box was taped shut and placed in a 28° C. incubator. The tiles were microscopically observed between 7–10 days after contact with the mold mixture for the presence or absence of fungal growth on the treated area and the results were reported using the following nomenclature: − =No Mold Growth, + =Growth Observed, and s=Uncertain Result. Three tiles were evaluated for each solution tested. The mold culture contained the following: *Penicillium commune, Phoma fimeti, Scolecobasidium humicola, Cladosporium cladosporioides, Pithomyces chartarum, Monilia grisea, Aureobasidium pullulans, Gliomastix cerealis, Alternaria alternata, Drechslera australiensis,* and *Aspergillus niger.*

In the "Torture Test Protocol", one drop (75 microliters) of the solution to be tested was placed in the center of the unglazed back side of a tile and allowed to dry for 5 minutes at room temperature (25° C.). The tile was then immediately rinsed with running tap water for 1.5 hours, allowed to dry overnight at room temperature, and was then exposed to the above-described mold culture as above and evaluated the same way as for the Standard Protocol. This test evaluates the speed of deposition of the organosilane from the aqueous solution.

The following Examples are merely illustrative of the present invention and are not to be considered as limiting the invention, which is properly delineated in the following claims. All parts and percentages expressed in the following Examples are by weight unless otherwise indicated.

In the Examples, the following ingredients were used:

ACRYLIC POLYMER EMULSION—An emulsion of a terpolymer of methacrylic acid/styrene/n-butyl acrylate in a 35/55/10 ratio at 25% nonvolative solids content, acid number of 226–236 (2 gram sample) and viscosity of less than 20 mPa. S.

ARQUAD® T-2C-50—A 50% actives blend of 1:1 by weight of tallowtrimethylammonium chloride and dicocodimethylammonium chloride from AKZO Chemicals, Inc.

BARDAC® 2250—Didecyldimonium chloride at 50% actives level from Lonza, Inc. of Fair Lawn, N.J.

BTAC—Benzyltrimethylammonium chloride at 50% actives level.

BTAH—Benzyltrimethylammonium hydroxide at 40% actives level.

DEGUSSA® -Silane Si 275—3-(triethoxysilyl)-propyldimethyloctadecyl ammonium chloride at 75% actives level in water/ethanol from Degussa Corporation of Ridgefield Park, N.J.

DEHYPON LS54—Fatty alcohol ethylene oxide and propylene oxide adduct from Henkel KGaA.

DERIPHAT® 151C—N-coco beta-amino propionic acid at 45% actives level from Henkel Corporation.

DOWANOL® PM—Methoxypropanol from Dow Chemical Company of Midland, Mich.

DOW CORNING® 5772—3-(trimethoxysilyl)-propyldimethyloctadecyl ammonium chloride at 72% actives level in methanol from Dow Corning Corp.

10% DOW CORNING® 5772—Solution of DOW CORNING® 5772 in water at 10% actives level and used immediately after preparation.

DOW CORNING® Z-6020—Aminoethylaminopropyltrimethoxysilane at 99% actives level from Dow Corning Corp.

DOW CORNING® Z-6070—Methyltrimethoxysilane at 98% actives level from Dow Corning Corp.

DOW CORNING® Z-6076—3-chloropropyltrimethoxysilane at 98% actives level from Dow Corning Corp.

EDTA—Ethylene diamine tetraacetic acid, tetrasodium salt, 40% in water.

EMPIGEN® BAC—Benzalkonium chloride at 50% actives level from Albright & Wilson Ltd., Detergent Group, of Whitehaven, Cumbria, England.

ICONOL® DA-6—Ethoxylated $C_{10}$ alcohol containing 6 moles of ethylene oxide per molecule from BASF Corporation.

ICONOL® DA-9—Ethoxylated $C_{10}$ alcohol containing 9 moles of ethylene oxide per molecule from BASF Corporation.

LUTENSOL® AO 8—Ethoxylated $C_{13}$-$C_{15}$ alcohol containing 8 moles of ethylene oxide per molecule from BASF AG.

LUTENSOL® ON30—Synthetic $C_{10}$ Oxo-alcohol containing 3 moles of ethylene oxide per molecule from BASF AG.

LUTENSOL® ON70—Synthetic $C_{10}$ Oxo-alcohol containing 7 moles of ethylene oxide per molecule from BASF AG.

NATROSOL® 250HHR—Hydroxyethylcellulose from Aqualon Company of Wilmington, Del.

NTA—Trisodium Nitrilotriacetate Monohydrate, Crystals, from W. R. Grace & Company.

Petrarch T2925—N-trimethoxysilylpropyl-N,N,N-trimethyl ammonium chloride at 50% actives level in methanol from Petrarch Systems.

REQUAT® Antimicrobial 1977 Liquid—3-(trimethoxysilyl)propylmethyldi(decyl) ammonium chloride at 45% actives level in methanol from Sanitized, Inc. (hereinafter "REQUAT® 1977") 16% REQUAT® 1977—Solution of REQUAT® 1977 in water at 16% actives level and used immediately after preparation.

SURFYNOL® 104H—Tetramethyl decynediol from Air Products & Chemicals, Inc. of Allentown, Pa.

TWEEN® 20—Polysorbate 20 from ICI Americas, Inc.

VELVETEX® BK-35—Cocamidopropyl betaine at 35% actives level from Henkel Corporation of Ambler, Pa.

EXAMPLES 1–3

These Examples demonstrate the production of aqueous disinfectant solutions according to the present invention. The compositions, in parts by weight, were as follows:

| Examples: | 1 | 2 | 3 |
| --- | --- | --- | --- |
| Deionized Water | 91.871 | 96.833 | 96.843 |
| Citric Acid (anhydrous) | 0.640 | — | — |
| Sodium Hydroxide | 0.339 | — | — |
| EDTA (40% in water) | 0.100 | 0.100 | 0.100 |
| EMPIGEN® BAC | 2.250 | 0.400 | 0.300 |
| LUTENSOL® AO 8 | 2.000 | — | — |
| ICONOL® DA-6 | — | 1.000 | 1.000 |
| ICONOL® DA-9 | — | 0.667 | 0.667 |
| DEHYPON® LS54 | — | 0.400 | 0.400 |
| SURFYNOL® 104H | — | 0.050 | 0.050 |
| DOW CORNING® 5772 | 0.150 | 0.150 | — |
| REQUAT® 1977 | — | — | 0.240 |
| DOWANOL® PM | 2.500 | — | — |
| Fragrance | — | 0.400 | 0.400 |
| Sodium Carbonate (10% in water) | 1.500 | — | — |
| pH | 9.0 | 5.0 | 5.0 |

Example 1 was made as follows: The ingredients were blended in the order listed with good stirring. The final pH was adjusted to 9.0 by the addition of 0.15 parts of sodium carbonate which was added as a 10% aqueous solution.

Example 2 was made as follows: The following ingredients were added to 85% of the amount of water and agitated (stirred with a paddle stirrer) until a clear solution was obtained: EDTA, ICONOL® DA-6, ICONOL® DA-9, DEHYPON® LS54, EMPIGEN® BAC and SURFYNOL® 104H. The fragrance was then added to the resulting solution and agitated to obtain a clear solution. The DOW CORNING® 5772 was added to the remaining 15% of the water in a separate container and agitated until it was completely dissolved. The water solution of the DOW CORNING® 5772 was added to the other solution and agitated until a clear aqueous solution was obtained. The pH of the solution was checked with a calibrated pH meter. The pH was adjusted to be from 4.5 to 5.5 with 0.1N aqueous hydrochloric acid if the initial pH was greater than 5.5.

Example 3 was made according to the same procedure described for Example 2, except the amount of REQUAT® 1977 noted above was substituted for the DOW CORNING® 5772 used in Example 2.

Each of the resulting aqueous solutions rendered the surface of a substrate such as unglazed ceramic tile antimicrobial using the Standard Protocol of the Residual Antimicrobial Mold Test.

EXAMPLES 4–6

These Examples demonstrate aqueous compositions which can be used as antimicrobial hand cleaner formulations:

| Examples: | 4 | 5 | 6 |
|---|---|---|---|
| DOW CORNING® 5772 | — | 0.15 | — |
| REQUAT® 1977 | — | — | 0.24 |
| VELVETEX® BK-35 (35%) | 5.00 | 5.00 | 5.00 |
| BARDAC® 2250 | 1.50 | 1.50 | 1.50 |
| Chlorhexidine Digluconate | 2.50 | 2.50 | 2.50 |
| Deionized Water | 91.00 | 90.85 | 90.76 |
| Sodium Hydroxide (1 N, aqueous) | 0.20 | 0.18 | 0.20 |
| Total: | 100.20 | 100.18 | 100.20 |
| pH value | 7.24 | 6.70 | 6.55 |

Each composition was made by adding the listed ingredients to all of the water at room temperature, in the order listed above, and agitating the solution after each ingredient was added until a homogeneous solution was obtained before the next ingredient was added. The pH was then adjusted with the 1N sodium hydroxide to a nominal pH of 6.7 with the final pH obtained being reported above. Example 4 was a comparative Example since it did not contain any organosilane. All solutions were observed to be clear initially and remained clear after 19 days of storage at room temperature.

EXAMPLES 7–12

These Examples demonstrate the production of aqueous solutions containing organosilanes with antimicrobial properties for use as mouthwashes. Examples 7 and 9 are comparative examples.

| Examples: | 7 | 8 |
|---|---|---|
| Ethyl Alcohol (95%) | 22.00 | 22.00 |
| Glycerin, USP | 12.00 | 12.00 |
| Madras Peppermint Flavor | 0.20 | 0.20 |
| Cetyl Pyridinium Chloride Monohydrate (98%) | 0.20 | 0.20 |
| TWEEN® 20 | 0.50 | 0.50 |
| Sodium Hydroxide (0.1 N in water)* | 0.36 | 0.33 |
| Deionized Water | 65.08 | 64.93 |
| Saccharin | 0.02 | 0.02 |
| DOW CORNING® 5772 | — | 0.15 |
| Total: | 100.36 g. | 100.33 g. |
| pH value | 6.55 | 6.50 |

*Adjust to nominal pH of 6.5.

| Examples: | 9 | 10 |
|---|---|---|
| Ethyl Alcohol (95%) | 22.00 | 22.00 |
| Glycerin, USP | 12.00 | 12.00 |
| Madras Peppermint Flavor | 0.20 | 0.20 |
| Cetyl Pyridinium Chloride Monohydrate (98%) | 0.40 | 0.40 |
| TWEEN® 20 | 0.50 | 0.50 |
| Sodium Hydroxide (0.1 N in water)* | 0.37 | 0.33 |
| Deionized Water | 64.88 | 64.73 |
| Saccharin | 0.02 | 0.02 |
| DOW CORNING® 5772 | — | 0.15 |
| Total: | 100.37 g. | 100.33 g. |
| pH value | 6.72 | 6.53 |

*Adjust to nominal pH of 6.5.

Each composition was made by adding the glycerine, cetyl pyridinium chloride, TWEEN® 20, saccharin and, if used, DOW CORNING® 5772 to the water followed by agitation to mix the ingredients together at room temperature. The flavor was added to the ethyl alcohol and agitated until it was dissolved. The ethanolic solution of flavoring was then added to the other solution with agitation and the pH was adjusted to a nominal value of 6.5 using the sodium hydroxide solution.

All compositions were clear solutions initially. Examples 7 and 8 appeared to be very slightly hazy after 24 hours at room temperature. Examples 9–10 retained their initial clarity after 24 hours at room temperature. No change in appearance was noted when the samples were observed after 6 days at room temperature. Example 9 remained clear after 20 days storage at room temperature. Example 10 was very slightly hazy after 20 days storage at room temperature. The higher level of cetylpyridinium chloride appeared to assist in rendering the compositions of Examples 9–10 more stable than Examples 7–8 based on the solution appearance.

Example numbers 11–12 were not used.

EXAMPLES 13–20

These Examples illustrate the long term stability of aqueous solutions prepared according to the present invention. A "BASE" composition was prepared composed of the following ingredients in parts with percentages listed parenthetically: deionized water 1119.30 (93.275%), NATROSOL® 250 HHR 3.30 (0.275%), EDTA (40% in water) 1.20 (0.100%), ICONOL® DA-9 3.96 (0.330%), ICONOL® DA-6 8.04 (0.670%), DEHYPON® LS54 4.80 (0.400%), EMPIGEN® BAC (50%) 54.00 (4.500%), SURFYNOL® 104H 0.60 (0.050%) and fragrance 4.80 (0.400%). Examples 13–20 were prepared by adding either DOW CORNING® 5772 ("DC 5772") or REQUAT® 1977 to the BASE as follows:

| Examples | BASE | DC 5772 | REQUAT® 1977 |
|---|---|---|---|
| 13 | 99.00 | 1.00 | — |

-continued

| Examples | BASE | DC 5772 | REQUAT ® 1977 |
|---|---|---|---|
| 14 | 99.50 | 0.50 | — |
| 15 | 99.75 | 0.25 | — |
| 16 | 99.90 | 0.10 | — |
| 17 | 99.95 | 0.05 | — |
| 18 | 99.36 | — | 0.64 |
| 19 | 99.68 | — | 0.32 |
| 20 | 99.84 | — | 0.16 |

The pH and clarity of each Example was observed initially and after 9 months storage at room temperature. The results are reported below:

| Examples | Initial pH | Initial Clarity | 9 Mo. pH | 9 Mo. Clarity |
|---|---|---|---|---|
| 13 | 4.98 | clear | 4.62 | clear |
| 14 | 4.88 | clear | 4.57 | clear |
| 15 | 5.14 | clear | 4.74 | clear |
| 16 | 5.14 | clear | 4.69 | clear |
| 17 | 5.06 | clear | 5.06 | clear |
| 18 | 5.16 | clear | 4.85 | separated |
| 19 | 5.23 | clear | 4.8 | hazy |
| 20 | 4.65 | clear | 4.48 | clear |

The DOW CORNING ® 5772 showed very good stability over a 9 month period while the REQUAT ® 1977 appeared to Show instability at that time for Examples 18 and 19 although 9 months at room temperature is a very long time for solutions of such organosilanes to remain stable.

EXAMPLES 21-24

In these Examples, the stability of aqueous solutions made according to the present invention at pHs ranging from about 3 to 10 was tested My an accelerated aging test involving storage of the samples in a 40° C. oven for one, two and three months. The Residual Antimicrobial Mold Test was also performed on these samples. The base compositions had the following formulas:

| Examples: | 21 | 22 | 23 | 24 |
|---|---|---|---|---|
| Deionized Water | 95.308 | 95.583 | 95.308 | 95.583 |
| 10% DOW CORNING ® 5772 | 1.500 | 1.500 | — | — |
| 16% REQUAT ® 1977 | — | — | 1.500 | 1.500 |
| NATROSOL ® 250 HHR | 0.275 | — | 0.275 | — |
| EDTA (40% in water) | 0.100 | 0.100 | 0.100 | 0.100 |
| ICONOL ® DA-6 | 1.000 | 1.000 | 1.000 | 1.000 |
| ICONOL ® DA-9 | 0.667 | 0.667 | 0.667 | 0.667 |
| DEHYPON ® LS54 | 0.400 | 0.400 | 0.400 | 0.400 |
| EMPIGEN ® BAC | 0.300 | 0.300 | 0.300 | 0.300 |
| SURFYNOL ® 104H | 0.050 | 0.050 | 0.050 | 0.050 |
| Fragrance | 0.400 | 0.400 | 0.400 | 0.400 |
| Total: | 100.000% | 100.000% | 100.000% | 100.000% |

An aliquot of each base composition was adjusted to a nominal pH of 3, 4, 5, 6, 7, 8, 9, and 10 using either aqueous hydrochloric acid or sodium hydroxide and divided into three equal portions, one to be opened at the end of each time period measured. The resulting samples were numbered Example 21.3 for the aliquots of base Example 21 having a nominal pH of 3, Example 21.4 for the aliquots of Example 21 having a nominal pH of 4 and so forth. The exact nominal pH was not obtained in all cases. The initial pH and the pH values of the Examples after 1, 2 and 3 months of storage at 40° C. plus the solution appearance abbreviated C=Clear, SH=Slightly Hazy, H=Hazy, S=Separated, CY=-Clear, but Yellowed, and HY=Hazy, but Yellowed is reported below:

| Examples: | | | |
|---|---|---|---|
| Init. pH | 1 Month | 2 Months | 3 Months |
| 21.3 3.32/C | 3.31/C | 3.35/C | 3.34/C |
| 21.4 4.00/C | 3.95/C | 3.94/C | 3.97/C |
| 21.5 4.78/C | 4.46/C | 4.42/C | 4.40/C |
| 21.6 5.45/C | 4.97/C | 4.84/C | 4.86/C |
| 21.7 6.81/C | 6.26/S | 6.23/SH | 6.34/C |
| 21.8 7.90/C | 6.94/S | 6.83/SH | 6.83/C |
| 21.9 9.21/C | 7.92/S | 7.69/S | 7.54/H |
| 21.10 9.87/C | 8.49/S | 8.17/S | 7.96/S |
| 22.3 2.68/C | 2.87/C | 2.89/C | 2.91/C |
| 22.4 3.67/C | 3.72/C | 3.68/C | 3.69/C |
| 22.5 5.34/C | 4.90/C | 4.87/C | 4.85/C |
| 22.6 5.57/C | 5.04/C | 4.98/C | 5.00/C |
| 22.7 6.98/C | 6.62/C | 6.52/C | 6.49/C |
| 22.8 7.22/C | 6.87/C | 6.76/C | 6.65/C |
| 22.9 9.34/C | 8.01/C | 7.90/C | 7.79/C |
| 22.10 10.03/C | 8.75/SH | 8.57/C | 8.32/C |
| 23.3 3.20/C | 3.20/C | 3.24/C | 3.23/C |
| 23.4 4.40/C | 4.33/C | 4.28/C | 4.34/C |
| 23.5 5.16/C | 4.88/C | 4.85/C | 4.85/C |
| 23.6 6.34/C | 5.88/S | 5.92/S | 5.99/H |
| 23.7 7.37/C | 6.90/S | 6.92/S | 7.03/S |
| 23.8 8.48/C | 7.70/S | 7.41/S | 7.30/S |
| 23.9 9.35/C | 8.22/S | 7.92/H | 7.69/H |
| 23.10 10.26/C | 9.27/S | 9.05/HY | 8.84/CY |
| 24.3 3.06/C | 3.05/C | 3.10/C | 3.05/C |
| 24.4 4.18/C | 4.11/C | 4.14/C | 4.11/C |
| 24.5 5.19/C | 4.90/C | 4.81/C | 4.80/C |
| 24.6 6.07/C | 5.51/C | 5.50/C | 5.67/C |
| 24.7 6.45/C | 5.97/C | 6.41/C | 6.55/C |
| 24.8 8.10/C | 7.45/C | 7.39/C | 7.38/C |
| 24.9 9.00/C | 7.79/C | 7.69/C | 7.62/C |
| 24.10 10.18/C | 9.06/C | 8.64/HY | 8.40/CY |

Thus, the samples containing the NATROSOL ® 250 HHR thickening agent tended to show some separation at the higher pH level and the pH tended to drop with time at the accelerated storage conditions studied. Examples 22 and 24 tended to remain clear across the pH range studied except for Example 22.10 which was slightly hazy at 1 month, but the other samples were clear after 2 and 3 months.

The Residual Antimicrobial Mold Test was run on the samples that were stored for 1, 2 and 3 months at 40° C. The negative control of an untreated ceramic tile gave a reading of +++, i.e., + for each tile tested. The positive control was three tiles treated with a fresh aqueous solution of 0.1% DOW CORNING ® 5772 and was rated −,−,−, i.e., no growth of mold observed on any tile.

For the Standard Protocol, the only sample which did not receive a − − − rating after 1 month at 40 ° C. was Example 21.9: −s− which is very close to being − − −. For the Standard Protocol, the only samples which did not receive a − − − rating after 2 months at 40 C° . were Example 21.7: s− −; and Example 22.3: s++. For the Standard Protocol, the only samples which did not receive a − − − rating after 3 months at 40 ° C. were Example 24.8: s− —; Example 24.9: +ss; and Example 24.10: s++.

The Torture Test Protocol was only run on the samples after 3 months at 40 ° C. Of these, the only samples which did not receive a − − − rating Example 23.10: ++s; Example 24.9: s− —; and Example 24.10: +++.

The results of this testing shows that the solutions tended to retain their ability to render substrates antimicrobial upon accelerated aging testing except at the very highest pH ranges for Examples 23 and 24 containing REQUAT® 1977 after 3 months of storage at 40° C.

EXAMPLE 25

In this comparative Example, the stability of an aqueous solution of REQUAT® 1977 across the pH range of from about 1 to 10 was studied. The samples were labelled as in Examples 21-24 where the sample with pH of 1 was labelled Example 25.1 and the like.

A base solution composed of 1197.12 parts of deionized water (99.76%) and 2.88 parts of REQUAT® 1977 (0.24%) was first prepared at room temperature. Then, 12.8 parts of 1N aqueous hydrochloric acid solution was added at room temperature to 120 parts of the base solution to obtain Example 25.1 which had a pH of 1.11. Example 25.2 was 120 parts of base solution and 1.26 parts of 1N hydrochloric acid and had a pH of 2.05. Example 25.3 was 120 parts of base solution and 0.12 parts of 1N hydrochloric acid and had a pH of 3.06. Example 25.4 was 120 parts of the base solution with a pH of 4.23. Example 25.5 was 120 parts of base solution and 0.05 parts of 1N aqueous sodium hydroxide and had a pH of 4.94. Example 25.6 was 120 parts of base solution and 0.06 parts of 1N sodium hydroxide and had a pH of 5.93. Example 25.7 was 120 parts of base solution and 0.08 parts of 1N sodium hydroxide and had a pH of 6.73. Example 25.8 was 120 parts of base solution and 0.12 parts of 1N sodium hydroxide and had a pH of 7.97. Example 25.9 was 120 parts of base solution and a sufficient amount of 1N sodium hydroxide to obtain a pH of 9.22. Example 25.10 was 120 parts of base solution and 0.24 parts of 1N sodium hydroxide and had a pH of 10.03.

Initially, the only clear solutions were Examples 25.2 and 25.3. All the other Examples appeared cloudy with Example 25.4 being the least cloudy.

After 24 hours at room temperature, Examples 25.2 and 25.3 remained clear and all others remained cloudy. The same results were observed for the samples which were stored at 40° C. for 24 hours although a faint ring was observed on the glass at the liquid level line.

After 48 hours at room temperature, Example 25.1 had a white layer was forming at the top of the liquid. Example 25.2 was clear (but slightly hazy when compared with Example 25.3), but had small white particles suspended throughout. Example 25.3 was clear, but had very tiny white particles suspended throughout the liquid. Examples 25.4 through 25.10 were cloudy, had a white ring on the inside of the glass bottle at the liquid level and had a small white layer forming on the top.

After 48 hours at 40° C., Example 25.1 appeared cloudy, had a white ring on the inside of the glass bottle at the liquid level and had a small white layer forming on the top. Example 25.2 was hazy, had a white ring on the inside of the glass bottle at the liquid level and had a small layer on top of the liquid. Example 25.3 was hazy, had a white ring on the inside of the glass bottle at the liquid level and a small layer was forming on the top. Examples 25.4 through 25.10 all appeared cloudy, all had a ring on the inside of the glass bottle at the liquid level and all had a small layer forming on top of the liquid as well as white particles on the bottom of the samples.

These aqueous solutions had very limited shelf stability as compared with the solutions described in Examples 21-24.

EXAMPLES 26-29

These Examples demonstrate the use of different organosilanes in the present invention.

| Examples: | 26 | 27 | 28 | 29 |
|---|---|---|---|---|
| Deionized Water-1 | 164.600 | 164.600 | 164.600 | 164.600 |
| Deionized Water-2 | 28.766 | 28.766 | 28.766 | 28.766 |
| DOW CORNING ® Z-6020 | 1.000 | — | — | — |
| DOW CORNING ® Z-6070 | — | 1.000 | — | — |
| DOW CORNING ® Z-6076 | — | — | 1.000 | — |
| Petrarch T2925 | — | — | — | 1.000 |
| EDTA (40% in water) | 0.200 | 0.200 | 0.200 | 0.200 |
| ICONOL ® DA-6 | 2.000 | 2.000 | 2.000 | 2.000 |
| ICONOL ® DA-9 | 1.334 | 1.334 | 1.334 | 1.334 |
| DEHYPON ® LS54 | 0.800 | 0.800 | 0.800 | 0.800 |
| EMPIGEN ® BAC | 0.800 | 0.800 | 0.800 | 0.800 |
| SURFYNOL ® 104H | 0.100 | 0.100 | 0.100 | 0.100 |
| Fragrance | 0.400 | 0.400 | 0.400 | 0.400 |
| 1 N Aqueous HCl | NR* | 0.520 | 0.520 | 0.550 |
| Total: | 200.000 | 200.520 | 200.520 | 200.550 |
| pH | 4.85 | 4.88 | 5.04 | 5.13 |

*NR = Not Recorded

Each Example was made by adding the EDTA, ICONOL® DA-6, ICONOL® DA-9, DEHYPON® LS54, EMPIGEN® BAC, SURFYNOL® 104H, and fragrance to the Deionized Water-1 with agitation until the solution became clear. The organosilane was added to the Deionized Water-2 in a separate container and mixed until it was completely dissolved. Thee aqueous organosilane solution was then added to the other aqueous solution with agitation. The pH was then adjusted with the hydrochloric acid solution to obtain a pH of between 4.5 and 5.5. Only Example 28 was observed to be slightly turbid in appearance while the other solutions were clear.. Example 29 left an antimicrobial film on ceramic tile when it was evaluated according to the Residual Antimicrobial Mold Test after treating the surface of three ceramic tiles each with 75 microliters of freshly prepared Example 29 and allowing it to dry for 5 minutes before the treated tile was washed with tap water for 30 minutes.

After one month storage at room temperature, Examples 26, 27 and 29 were observed as being stable and clear while Example 28 was unstable. After 7 weeks at room temperature, Examples 26, 27 and 29 were clear solutions while Example 28 appeared translucent with some settling on the bottom. Example 28 contained 3-chloropropyltrimethoxysilane which did not appear to be sufficiently water soluble to be useful in the present method.

Examples 26-29 were each applied to one half of a glass plate to check ability to render the surface hydrophobic and thus to cause water to bead away from the treated side. This beading was observed after the glass plate was rinsed with water to remove any residual surfactants present in the resulting film. Each of Examples 26-29 appeared to deposit rinse-resistant films of organosilane on the glass plate. Examples 26 and 27 did not cause any noticeable water beading effect after a small portion of each composition was added to the glass plate using a pipette. Examples 28 and 29 did result in noticeable water beading. The water beading effect only persisted for about 2 rinses with water for Example 29. Only Example 29 appeared to impart some scratch resistance to the glass plate. The other Examples 26-28 were either the same as the untreated side in scratch resistance to sandpaper or were slightly easier to scratch.

EXAMPLE 30

In this comparative Example, a water insoluble quaternary ammonium functional organosilane was tried, 3-(triethoxysilyl)propyldimethyloctadecyl ammonium chloride, but it did not form a solution when processed according to the present invention. Example 30 had the same formulation as did Example 26, except 1.000 part of DEGUSSA ® -Silane Si 275 was substituted for the DOW CORNING ® Z-6020 used in Example 26.

Example 30 was made as in Example 26 by adding the EDTA, ICONOL ® D A-6, ICONOL ® D A-9, DEHYPON ® LS54, EMPIGEN ® BAC, SURFYNOL ® 104H, and fragrance to the Deionized Water-1 with agitation until the solution became clear. However, when the organosilane was added to the Deionized Water-2 in a separate container, it was insoluble in the water. The aqueous organosilane was then added to the other aqueous solution with agitation, but it still did not become soluble. The resulting composition was not deemed to be useful.

EXAMPLES 31-34

These Examples show formulations useful as disinfecting carpet shampoos which employ amphoteric and sarcosinate surfactants. Examples 33-34 further contain a carboxylated polymer used as an antisoil agent.

The formulations were as follows:

| Examples: | 31 | 32 | 33 | 34 |
| --- | --- | --- | --- | --- |
| Deionized Water | 94.80 | 94.80 | 83.52 | 83.52 |
| Sodium Lauroyl Sarcosinate (30% actives) | 2.50 | 2.50 | 2.50 | 2.50 |
| EDTA (40% in water) | 0.10 | 0.10 | 0.10 | 0.10 |
| EMPIGEN ® BAC | 0.25 | 0.25 | 0.25 | 0.25 |
| DOWANOL ® PM | 2.00 | 2.00 | 2.00 | 2.00 |
| DERIPHAT ® 151C | 0.10 | 0.10 | 0.10 | 0.10 |
| Acrylic Polymer Emulsion | — | — | 11.28 | 11.28 |
| Citric Acid (10%, aqueous) | to pH 6 | — | to pH 6 | — |
| Sodium Bicarbonate (10%, aqueous) | — | to pH 9 | — | to pH 9 |
| DOW CORNING ® 5772 | 0.25 | 0.25 | 0.25 | 0.25 |

After three weeks of storage at room temperature, each of Examples 31-34 exhibited deposition of organosilane onto a glass plate as evidenced by rinse-resistant water beading from the treated surface.

After three weeks at room temperature, each of Examples 31-34 was stable and no haziness or separation was noted.

EXAMPLES 35-42

In these Examples, aqueous solutions were prepared according to the present invention (Examples 37-40) and for comparative purposes: Examples 35-36 without water soluble quaternary ammonium compound or water soluble organosilane and Examples 41-42 without water soluble quaternary ammonium compound.

To prepare these Examples, four Base compositions were prepared having the following formulations in parts:

| | BASE A | BASE B | BASE C | BASE D |
| --- | --- | --- | --- | --- |
| Deionized Water | 1161.3 | 1157.7 | 1168.6 | 1165.0 |

-continued

| | BASE A | BASE B | BASE C | BASE D |
| --- | --- | --- | --- | --- |
| NATROSOL ® 250 HHR | 3.3 | 3.3 | — | — |
| EDTA (40% in water) | 1.2 | 1.2 | 1.2 | 1.2 |
| ICONOL ® DA-6 | 12.0 | 12.0 | 12.0 | 12.0 |
| ICONOL ® DA-9 | 8.0 | 8.0 | 8.0 | 8.0 |
| DEHYPON ® LS54 | 4.8 | 4.8 | 4.8 | 4.8 |
| EMPIGEN ® BAC | — | 3.6 | — | 3.6 |
| SURFYNOL ® 104H | 0.6 | 0.6 | 0.6 | 0.6 |
| Fragrance | 4.8 | 4.8 | 4.8 | 4.8 |
| pH | 5.39 | 5.37 | 5.06 | 5.26 |

BASE A and BASE B were each prepared by first mixing the water with the NATROSOL ® 250 HHR with a paddle stirrer for 4 hours at room temperature to obtain a homogeneous, thickened solution. The remaining ingredients were added to that solution in the order listed and allowed to stir until the mixture was homogeneous. The pH was adjusted with 1N aqueous hydrochloric acid. BASE C and BASE D were prepared by adding the ingredients together in the order listed using a magnetic stirring bar stirrer. The pH of each was adjusted with 1N aqueous hydrochloric acid.

Examples 35-42 were prepared using the above Bases plus either DOW CORNING ® 5772 or REQUAT ® 1977 for some of the Examples using dilute, freshly prepared aqueous solutions of those water soluble quaternary ammonium organosilanes by simply stirring the aqueous organosilane solution into an aliquot of base using a magnetic stirring bar. No high shear mixers or homogenizer apparatus were used to prepare any of Examples 35-42. The formulations used were:

| Examples: | 35 | 36 | 37 | 38 |
| --- | --- | --- | --- | --- |
| BASE A | 40.0 | — | — | — |
| BASE B | — | — | 39.4 | — |
| BASE C | — | 40.0 | — | — |
| BASE D | — | — | — | 39.4 |
| 10% DOW CORNING ® 5772 | — | — | — | — |
| 16% REQUAT ® 1977 | — | — | 0.6 | 0.6 |
| Mean Particle Diameter (microns) | 33/1000* | 145 | 8 | 6 |
| Polydispersity Index (Q) | 0.2/1.7* | 0.3 | 0.3 | 0.3 |

*First figure is clear, subnatant layer, second figure is after 2 phase composition was mixed together by stirring.

| Examples: | 39 | 40 | 41 | 42 |
| --- | --- | --- | --- | --- |
| BASE A | — | — | 39.4 | — |
| BASE B | 39.4 | — | — | — |
| BASE C | — | — | — | 39.4 |
| BASE D | — | 39.4 | — | — |
| 10% DOW CORNING ® 5772 | 0.6 | 0.6 | 0.6 | 0.6 |
| 16% REQUAT ® 1977 | — | — | — | — |
| Mean Particle Diameter (microns) | 13 | 5 | 1300 | 250 |
| Polydispersity Index (Q) | 0.5 | 0.3 | 1.5 | 0.3 |

After each Example was prepared, each composition was studied at 25° C. using a quasielastic light scattering instrument called a Brookhaven ™ Photon Correlation Spectrometer from Brookhaen Instruments Corporation fitted with a BI2030 Digital Correlator and an argon ion laser. The measured autocorrelation functions obtained for each Example were analyzed using the method of cummulants described in the Digital Correlator Operator Manual from Brookhaven Instruments, 1990, to obtain a mean particle diameter and a relative variance or polydispersity value (Q). Generally, a value of Q less than 0.2 indicates a low degree of polydispersity of particles in the sample. Additionally, data obtained from the samples of each Example tested were subjected to an inverse Laplace transform analysis using an algorithm ("CONTIN") to obtain the mean particle size distribution reported below the formulations for each Example.

Comparative Examples 35 and 36 had larger particle sizes relative to Examples 37–40 representing the present invention. Example 35, which contained NATROSOL® 250 HHR thickener, separated into two layers and measurements of mean particle size and polydispersity were made both on the clear subnatant layer and after simply stirring the sample to disperse the two layers together.

Inventive Examples 37–40 all formed clear solutions containing small mean particle sizes and low Q values indicating a low degree of polydispersity. These solutions with very small particle sizes might be called microemulsions, but the important fact is that no high shear homogenization techniques were needed to prepare them. Unlike Example 35, there was no separation of Examples 37 and 39 which also contained NATROSOL® 250 HHR.

Examples 41 and 42 were prepared to determine if the DOW CORNING® 5772 would act in conjunction with the other surfactants present, but without the water soluble quaternary ammonium compound, to produce the aqueous solutions of the present invention using the same low shear mixing techniques used in Examples 35–40. Example 41, which included NATROSOL® 250 HHR, produced a very large mean particle size product which a relatively high polydispersity value. Example 42, without NATROSOL® 250 HHR, gave a much higher mean average particle size product of 250 microns even though the polydispersity value was on the same order as Examples 37–40.

Thus, the presence of water soluble organosilane, the water soluble organic quaternary ammonium compound and the additional surfactants appear to be necessary to the present invention.

EXAMPLES 43–46

In these Examples, the three ingredients used in Sample III, Table I of U.S. Pat. No. 4,847,088 were used to form aqueous organosilane solutions and the storage stability of each solution was evaluated. The solutions prepared were as follows:

| Examples: | 43 | 44 | 45 | 46 |
|---|---|---|---|---|
| Deionized Water | 98.00 | 98.85 | 96.85 | 94.85 |
| ARQUAD® T-2C-50 (50%) | 1.00 | 1.00 | 3.00 | 5.00 |
| SYLGARD® 5772 (72%) | 1.00 | 0.15 | 0.15 | 0.15 |
| Total: | 100.00 | 100.00 | 100.00 | 100.00 |
| pH: | 4.93 | 4.39 | 4.63 | 4.67 |
| Appearance on Mixing | C/WW | C/WW | C/VPY | C/VPY |
| Storage at Room Temp. | | | | |
| 4.5 Weeks | C | C | C/VPY | C/VPY |
| Storage at 60° C. | | | | |
| 2 Days | C | C | C | C |
| 4.5 Weeks | C | C | C | C |

C = Clear
WW = Water White
VPY = Very Pale Yellow

All solutions were found to be stable and plate glass treated with samples of each of Examples 43–46 exhibited a water repellent coating on the glass. This was observed for samples stored at room temperature as well as those stored at 60° C. for at least 4.5 weeks. Nothing in the '088 Patent suggests that such solutions would be stable and the '088 Patent teaches that such solutions are not desirable in Table II due to a 75% fungal overgrowth of substrates treated with an aqueous solution containing the above ingredients.

EXAMPLES 47–58

In these Examples, various alkaline hard surface cleaner formulations were prepared over a pH range of from about 9 to 13 according to the present invention. The storage stability of each formulation was evaluated using accelerated aging at 40° C. and the ability of each formulation to render a tile substrate antimicrobial was evaluated after such accelerated aging.

The following stock solutions (in grams) were prepared:

| Examples: | 47 | 48 | 49 | 50 |
|---|---|---|---|---|
| Water - I | 758.795 | 737.545 | 695.045 | 771.545 |
| Water - II | 133.905 | 130.155 | 122.655 | 136.155 |
| DC 5772 | 1.500 | 1.500 | 1.500 | 1.500 |
| EDTA | 25.000 | 50.000 | 100.000 | 0.000 |
| NTA | 0.000 | 0.000 | 0.000 | 10.000 |
| ICONOL® DA-9 | 13.330 | 13.330 | 13.330 | 13.330 |
| ICONOL® DA-6 | 6.670 | 6.670 | 6.670 | 6.670 |
| Benzalkonium Chloride (50% actives) | 22.500 | 22.500 | 22.500 | 22.500 |
| Citric Acid (50% in water) | 12.800 | 12.800 | 12.800 | 12.800 |
| Fragrance | 0.500 | 0.500 | 0.500 | 0.500 |
| DOWANOL® PM | 25.000 | 25.000 | 25.000 | 25.000 |

| Examples: | 51 | 52 | 53 | 54 |
|---|---|---|---|---|
| Water - I | 763.045 | 746.045 | 694.620 | 673.370 |
| Water - II | 134.655 | 131.655 | 122.580 | 118.830 |
| DC 5772 | 1.500 | 1.500 | 1.500 | 1.500 |
| EDTA | 0.000 | 0.000 | 100.000 | 100.000 |
| NTA | 20.000 | 40.000 | 0.000 | 0.000 |
| ICONOL® DA-9 | 13.330 | 13.330 | 13.330 | 13.330 |
| ICONOL® DA-6 | 6.670 | 6.670 | 6.670 | 6.670 |
| Benzalkonium Chloride (50% actives) | 22.500 | 22.500 | 22.500 | 22.500 |
| Citric Acid (50% in water) | 12.800 | 12.800 | 12.800 | 12.800 |
| Fragrance | 0.500 | 0.500 | 1.000 | 1.000 |
| DOWANOL® PM | 25.000 | 25.000 | 25.000 | 50.000 |

| Examples: | 55 | 56 | 57 | 58 |
|---|---|---|---|---|
| Water - I | 630.870 | 745.620 | 724.370 | 681.870 |
| Water - II | 111.330 | 131.580 | 127.830 | 120.330 |
| DC 5772 | 1.500 | 1.500 | 1.500 | 1.500 |
| EDTA | 100.000 | 0.000 | 0.000 | 0.000 |
| NTA | 0.000 | 40.000 | 40.000 | 40.000 |
| ICONOL® DA-9 | 13.330 | 13.330 | 13.330 | 13.330 |
| ICONOL® DA-6 | 6.670 | 6.670 | 6.670 | 6.670 |
| Benzalkonium Chloride (50% actives) | 22.500 | 22.500 | 22.500 | 22.500 |
| Citric Acid (50% in water) | 12.800 | 12.800 | 12.800 | 12.800 |
| Fragrance | 1.000 | 1.000 | 1.000 | 1.000 |
| DOWANOL® PM | 100.000 | 25.000 | 50.000 | 100.000 |

Each stock solution was prepared by taking the Water-I and dissolving all of the other ingredients in the order listed, except for the DC 5772, into the Water-I with stirring. In a separate container, the DC 5772 was stirred into the Water-II to form a solution. The DC 5772 solution made with the Water-II was then quickly stirred into the solution made with the Water-I to form the stock solution.

Each of the above stock solutions was adjusted to a pH of 9 by the addition of anhydrous sodium carbonate. Two hundred milliliters ("ml") of the solution was divided into two 100 ml samples designated with the suffixes -9A and -9B, respectively, where the -9A samples were stored in sealed bottles at room temperature and the -9B samples were stored in sealed bottles at 40° C. The remaining solution was adjusted to a pH of 10 using anhydrous sodium carbonate and 200 ml of that solution was divided in two to produce samples with the suffix -10A and -10B as above. The remaining solution was adjusted to a pH of 11 using flaked sodium hydroxide (95%) and 200 ml of that solution was divided in two to produce samples with the suffix -11A and -11B as above. Additional sodium hydroxide was added to the remaining solution as above to obtain samples at a pH of 12 (suffixes -12A and -12B) and, finally, at a pH of 13 (suffixes -13A and -13B) as above.

The appearance of the samples stored at 40° C. after one month was as follows:

| Example | pH −9 (−9B) | pH −10 (−10B) | pH −11 (−11B) | pH −12 (−12B) | pH −13 (−13B) |
|---|---|---|---|---|---|
| 47 | C/WW | C/WW | C/WW | C/WW | * |
| 48 | C/WW | C/WW | C/SY | C/SY | C/Y |
| 49 | C/WW | C/WW | C/SY | C/SY | C/Y |
| 50 | C/WW | C/WW | C/SY | C/SY | C/Y |
| 51 | C/WW | C/SY | C/SY | C/SY | C/Y |
| 52 | C/WW | C/SY | C/SY | C/SY | C/Y |
| 53 | C/VSY | C/VSY | C/SY | C/SY | C/Y |
| 54 | C/WW | C/WW | C/WW | C/VSY | C/SY |
| 55 | C/WW | C/VSY | C/VSY | C/SY | C/Y |
| 56 | C/WW | C/VSY | C/VSY | C/SY | C/Y |
| 57 | C/WW | C/VSY | C/VSY | C/SY | C/Y |
| 58 | C/WW | C/VSY | C/VSY | C/SY | C/Y |

C = Clear
WW = Water White
VSY = Very Slightly Yellow
SY = Slightly Yellow
Y = Yellow
* = Yellow, Clear with Dark Yellow Top Layer The appearance of the above samples was again checked after two months at 40° C. All samples appeared clear with no visible separation except for Example 47-13B which had a darker brown layer at the top. The samples ranged in color from clear water white for the pH 9 samples to clear yellow for the highest pH 13 samples where the yellow color became darker with increasing pH value across each series of samples.

After one month at 40° C., the above samples were each tested for ability to treat glass with the organosilane as evidenced by water sheeting away from the treated glass surface. The test used 5 inch by 7 inch (12.7 cm by 17.8 cm) sheets of glass which were previously washed with AGREE® Shampoo from S. C. Johnson & Son, Inc., of Racine, Wis. and allowed to drip dry at room temperature. A pipette was used to add a small amount of the sample being tested to the glass and the plate was then rinsed with tap water. All of the aged samples exhibited a water sheeting effect indicating that a sufficient amount of active organosilane was present in each sample to bind to and treat the glass surface.

Also after one month storage time, the samples were tested according to a modification of the Residual Antimicrobial Mold Test using only *Aspergillus Niger* in the mold culture. The tiles used were the porous, non-glassy side of 0.75 inch by 1.0 inch (1.9 cm by 2.5 cm) ceramic tiles (done in triplicate for each sample) which were rinsed with running tap water for 1.5 hours and dried before one drop (75 microliters) of the sample being tested was added to the center of the tile. The drop was allowed to dry for five minutes at room temperature and then the tile was again rinsed with running tap water with the porous side up for 1.5 hours and then allowed to dry at room temperature overnight. All tiles tested (both room temperature and 40° C. storage) showed no growth except for the following samples which had been stored at room temperature: Example 49-9A: −−s; 50-13A: +s−; and 57-13A: −−s.

The above test was run on the samples after they were stored for two months at 40° C. The results were that all of the test tiles had a rating of "−" indicating no mold growth.

Thus, all of the Examples appeared to be sufficiently stable at relatively high pH values to retain their ability to treat surfaces with the organosilane.

EXAMPLES 59–72

In these Examples, several different quaternary ammonium compounds were evaluated at increasing levels in the method of the present invention as Examples 59–67. Examples 62–64 employ a very basic form of a quaternary ammonium compound, benzyltrimethylammonium hydroxide. Comparative Examples 68–72 omit the use of a basic quaternary ammonium compound and substitute sodium hydroxide in its place to obtain solutions with similar pH values.

The formulations and results are summarized below:

| Examples | 59 | 60 | 61 | 62 |
|---|---|---|---|---|
| Ingredients: | | | | |
| Deionized Water | 97.85 | 95.85 | 93.85 | 97.60 |
| LUTENSOL ® ON70 | 1.00 | 1.00 | 1.00 | 1.00 |
| BTAC | 1.00 | 3.00 | 5.00 | — |
| BTAH | — | — | — | 1.25 |
| EMPIGEN ® BAC | — | — | — | — |
| Sodium Hydroxide (100%) | — | — | — | — |
| DC 5772 | 0.15 | 0.15 | 0.15 | 0.15 |
| Total: | 100.00 | 100.00 | 100.00 | 100.00 |
| pH: | 5.46 | 5.69 | 6.43 | 11.75 |
| Appearance on Mixing | C | C | C | C |
| 6 Weeks at Room Temperature | C | C | C | C |
| Storage at 60 C. | | | | |
| 4 Hours | — | — | — | — |
| 1 Week | — | — | — | — |
| 2 Weeks | C | C | C | C |
| 6 Weeks | C | C | C | C |

C = Clear/Colorless
CL = Cloudy
W = White
H = Hazy
S = Separated

| Examples | 63 | 64 | 65 | 66 |
|---|---|---|---|---|
| Ingredients: | | | | |
| Deionized Water | 95.10 | 92.60 | 97.85 | 95.85 |
| LUTENSOL ® ON70 | 1.00 | 1.00 | 1.00 | 1.00 |
| BTAC | — | — | — | — |
| BTAH | 3.75 | 6.25 | — | — |
| EMPIGEN ® BAC | — | — | 1.00 | 3.00 |
| Sodium Hydroxide (100%) | — | — | — | — |
| DC 5772 | 0.15 | 0.15 | 0.15 | 0.15 |
| Total: | 100.00 | 100.00 | 100.00 | 100.00 |

-continued

| Examples | 63 | 64 | 65 | 66 |
|---|---|---|---|---|
| pH: | 12.41 | 12.58 | 5.23 | 5.5 |
| Appearance on Mixing | C | C | C | C |
| 6 Weeks at Room Temperature | C | C | C | C |
| Storage at 60 C. | | | | |
| 4 Hours | — | — | — | — |
| 1 Week | — | — | — | — |
| 2 Weeks | C | C | C | C |
| 6 Weeks | C | C | C | C |

C = Clear/Colorless
CL = Cloudy
W = White
H = Hazy
S = Separated

| Examples | 67 | 68 | 69 | 70 |
|---|---|---|---|---|
| Ingredients: | | | | |
| Deionized Water | 93.85 | 98.80 | 98.65 | 98.35 |
| LUTENSOL ® ON70 | 1.00 | 1.00 | 1.00 | 1.00 |
| BTAC | — | — | — | — |
| BTAH | — | — | — | — |
| EMPIGEN ® BAC | 5.00 | — | — | — |
| Sodium Hydroxide (100%) | — | 0.05 | 0.20 | 0.50 |
| DC 5772 | 0.15 | 0.15 | 0.15 | 0.15 |
| Total: | 100.00 | 100.00 | 100.00 | 100.00 |
| pH: | 6.56 | 11.67 | 12.24 | 12.57 |
| Appearance on Mixing | C | C | C | C |
| 6 Weeks at Room Temperature | C | C | C | C |
| Storage at 60 C. | | | | |
| 4 Hours | — | — | — | — |
| 1 Week | — | — | — | — |
| 2 Weeks | C | C | C | C |
| 6 Weeks | C | C | C | C |

C = Clear/Colorless
CL = Cloudy
W = White
H = Hazy
S = Separated

| Examples | 71 | 72 |
|---|---|---|
| Ingredients: | | |
| Deionized Water | 97.35 | 96.35 |
| LUTENSOL ® ON70 | 1.00 | 1.00 |
| BTAC | — | — |
| BTAH | — | — |
| EMPIGEN ® BAC | — | — |
| Sodium Hydroxide (100%) | 1.50 | 2.50 |
| DC 5772 | 0.15 | 0.15 |
| Total: | 100.00 | 100.00 |
| pH: | 12.84 | 12.94 |
| Appearance on Mixing | C | C |
| 6 Weeks at Room Temperature | C | C |
| Storage at 60 C. | | |
| 4 Hours | — | H |
| 1 Week | H | — |
| 2 Weeks | H(S) | H(S) |
| 6 Weeks | — | — |

C = Clear/Colorless
CL = Cloudy
W = White
H = Hazy
S = Separated

In these Examples, the nonionic surfactant employed had an average of about 7 ethoxy groups per molecule making it relatively hydrophilic and thus, more water soluble. Examples 59-61 used the quaternary ammonium salt, benzyltrimethylammonium chloride, to obtain solutions of pH value between 5.4 and 6.5. All of these solutions were stable upon accelerated aging.

Examples 62-64 used the quaternary ammonium hydroxide analog of the quaternary ammonium salt used in Examples 59-61, benzyltrimethylammonium hydroxide, as the quaternary ammonium compound. These solutions were also found to be stable upon accelerated aging even though the pH of the solution was much higher at between 11.7 and 12.6. Examples 65-67 used benzalkonium chloride as the quaternary ammonium salt without any further pH adjustments. All three solutions were stable upon accelerated aging.

Comparative Examples 68-72 omitted the presence of any ammonium compound as a stabilizer. The solutions tended to become unstable with increasing amounts of sodium hydroxide such that Examples 71-72 at a pH of almost 13 were not stable very long upon accelerated aging. Examples 68-70 did exhibit deposition of organosilane on glass as evidenced by a water sheeting effect on treated areas of the glass after 6 weeks storage at 60° C.

EXAMPLES 73-86

In these Examples, the experiments in Examples 59-72 were repeated, but a less hydrophilic version of the nonionic surfactant used in those Examples was employed the nonionic surfactant only contained an average of only 3 ethoxy groups per molecule. Examples 73-78 and 82-86 are comparative Examples while Examples 79-81 are within the present invention. These Examples demonstrate the importance of water solubility or hydrophilicity in selecting the types and amounts of stabilizing quaternary ammonium compounds and according to the present invention.

The formulations used and the results were as follows:

| Examples | 73 | 74 | 75 | 76 |
|---|---|---|---|---|
| Ingredients: | | | | |
| Deionized Water | 97.85 | 95.85 | 93.85 | 97.60 |
| LUTENSOL ® ON30 | 1.00 | 1.00 | 1.00 | 1.00 |
| BTAC | 1.00 | 3.00 | 5.00 | — |
| BTAH | — | — | — | 1.25 |
| EMPIGEN ® BAC | — | — | — | — |
| Sodium Hydroxide (100%) | — | — | — | — |
| DC 5772 | 0.15 | 0.15 | 0.15 | 0.15 |
| Total: | 100.00 | 100.00 | 100.00 | 100.00 |
| pH: | 6.30 | 6.71 | 7.15 | 11.95 |
| Appearance on Mixing | CL/W | CL/W | CL/W | CL/W |
| Storage at Room Temperature | | | | |
| 4 Hours | S | S | S | S |
| 6 Weeks | S | S | S | S |
| Storage at 60 C. | | | | |
| 4 Hours | S | S | S | S |
| 2 Weeks | — | — | — | — |
| 6 Weeks | S | S | S | S |

C = Clear/Colorless
CL = Cloudy
W = White
H = Hazy
S = Separated

| Examples | 77 | 78 | 79 | 80 |
|---|---|---|---|---|
| Ingredients: | | | | |
| Deionized Water | 95.10 | 92.60 | 97.85 | 95.85 |
| LUTENSOL ® ON30 | 1.00 | 1.00 | 1.00 | 1.00 |
| BTAC | — | — | — | — |
| BTAH | 3.75 | 6.25 | — | — |
| EMPIGEN ® BAC | — | — | 1.00 | 3.00 |
| Sodium Hydroxide (100%) | — | — | — | — |
| DC 5772 | 0.15 | 0.15 | 0.15 | 0.15 |

| Examples | 77 | 78 | 79 | 80 |
|---|---|---|---|---|
| Total: | 100.00 | 100.00 | 100.00 | 100.00 |
| pH: | 12.89 | 12.90 | 5.38 | 6.30 |
| Appearance on Mixing | CL/W | CL/W | C | C |
| Storage at Room Temperature | | | | |
| 4 Hours | S | S | — | — |
| 6 Weeks | S | S | C | C |
| Storage at 60 C. | | | | |
| 4 Hours | S | S | — | — |
| 2 Weeks | — | — | C | C |
| 6 Weeks | S | S | C | C |

C = Clear/Colorless
CL = Cloudy
W = White
H = Hazy
S = Separated

| Examples | 81 | 82 | 83 | 84 |
|---|---|---|---|---|
| Ingredients: | | | | |
| Deionized Water | 93.85 | 98.80 | 98.65 | 98.35 |
| LUTENSOL ® ON30 | 1.00 | 1.00 | 1.00 | 1.00 |
| BTAC | — | — | — | — |
| BTAH | — | — | — | — |
| EMPIGEN ® BAC | 5.00 | — | — | — |
| Sodium Hydroxide (100%) | — | 0.05 | 0.20 | 0.50 |
| DC 5772 | 0.15 | 0.15 | 0.15 | 0.15 |
| Total: | 100.00 | 100.00 | 100.00 | 100.00 |
| pH: | 6.64 | 11.95 | 12.42 | 12.71 |
| Appearance on Mixing | C | CL/W | CL/W | CL/W |
| Storage at Room Temperature | | | | |
| 4 Hours | — | S | S | S |
| 6 Weeks | C | S | S | S |
| Storage at 60 C. | | | | |
| 4 Hours | — | S | S | S |
| 2 Weeks | C | — | — | — |
| 6 Weeks | C | S | S | S |

C = Clear/Colorless
CL = Cloudy
W = White
H = Hazy
S = Separated

| Examples | 85 | 86 |
|---|---|---|
| Ingredients: | | |
| Deionized water | 97.35 | 96.35 |
| LUTENSOL ® ON30 | 1.00 | 1.00 |
| BTAC | — | — |
| BTAH | — | — |
| EMPIGEN ® BAC | — | — |
| Sodium Hydroxide (100%) | 1.50 | 2.50 |
| DC 5772 | 0.15 | 0.15 |
| Total: | 100.00 | 100.00 |
| pH: | 13.19 | 13.19 |
| Appearance on Mixing | CL/W | CL/W |
| Storage at Room Temperature | | |
| 4 Hours | S | S |
| 6 Weeks | S | S |
| Storage at 60 C. | | |
| 4 Hours | S | S |
| 2 Weeks | — | — |
| 6 Weeks | S | S |

C = Clear/Colorless
CL = Cloudy
W = White
H = Hazy
S = Separated

None of the solutions prepared with benzyltrimethylammonium chloride (Examples 73–75) or benzyltrimethylammonium hydroxide (Examples 76–78) formed clear stable solutions. However, Examples 79–81 using benzalkonium chloride were all clear and stable, even upon accelerated aging. It was felt that this difference was due to the fact that benzalkonium chloride is more water soluble that benzyltrimethylammonium chloride. The greater degree of hydrophilicity exhibited by the benzalkonium chloride apparently overcomes the reduced hydrophilicity of the nonionic surfactant employed in these Examples to result in clear and stable solutions. An increase in the amount of nonionic surfactant present in the comparative Examples may also serve to render the solutions clear and stable.

Examples 82–86 were also unstable and demonstrate the effect of the hydropholicity of the nonionic surfactant on solution stability as compared with Examples 68–72.

Which we claim is:

1. A method of improving the storage stability and broadening the pH stability of an aqueous solution containing from about 0.001% to 5% by weight of a water soluble organosilane of the formula $$A_{3-x}B_xSiD$$

provided that the organosilane forms a clear solution in water at 25° C. at the intended level of use, which method comprises including within the solution
   a. from about 0.05% to 10% by weight of the total aqueous solution of a water soluble organic quaternary ammonium compound which is free of silicon atoms and contains at least one nitrogen-bonded hydrocarbon group of at least 8 carbons and
   b. from about 0.5% to 30% by weight of the total aqueous solution of at least one surfactant selected from the group consisting of nonionic, amphoteric, sarcosine anionic, and cationic surfactants other than the compounds of (a);
wherein the amounts of (a) and (b) present are effective to improve the storage stability of and to broaden the pH stability of the resulting solution and each
   A is —OH or a hydrolyzable group,
   B is an alkyl group of from 1 to 4 carbon atoms,
   x has a value of 0, 1 or 2, and
   D is a hydrocarbon group of from 1 to 4 carbon atoms, phenyl, or a nonionic or cationic, substituted-hydrocarbon group containing at least one oxygen or nitrogen group or salts of such substituted-hydrocarbon groups.

2. The method as claimed in claim 1 wherein (a) is a water soluble organic quaternary ammonium salt.

3. The method as claimed in claim 2 wherein A is selected from the group consisting of —OR$^1$ and —OR$^{24}$OR$^1$ where each R$^1$ is R$^2$ or hydrogen, R$^2$ is an alkyl group of 1 to 4 carbon atoms, R$^{24}$ is a divalent saturated hydrocarbon group of from 1 to 4 carbon atoms and x has a value of 0 or 1.

4. The method as claimed in claim 3 wherein D is selected from the group consisting of alkyl groups of from 1 to 4 carbon atoms, vinyl, allyl, glycidoxypropyl, —R$^3$N(R$^4$)$_y$H$_{2-y}$, —R$^3$N$^{(+)}$(R$^4$)$_y$H$_{3-y}$X$^{(-)}$, —R$^3$NHR$^3$N(R$^4$)$_y$H$_{2-y}$, —R$^3$NHR$^3$N$^{(+)}$(R$^4$)$_y$H$_{3-y}$X$^{(-)}$, —R$^3$N$^{(+)}$R$^2$R$^4$R$^5$X$^{(-)}$ and

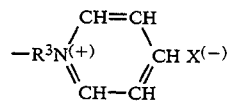

wherein
R³ is a divalent saturated hydrocarbon group of from 1 to 12 carbon atoms; R⁴ and R⁵ are each selected from the group consisting of alkyl groups of 1 to 18 carbon atoms, —CH₂C₆H₅, —CH₂CH₂OH and —CH₂OH;
y has a value of 0, 1 or 2; and
X is an anion.

5. The method as claimed in claim 4 wherein the water soluble organic quaternary ammonium compound is selected from the group consisting of R⁷R⁸N(+)(R²)₂X(−) and C₅H₅N(+)R⁷X(−) wherein
R⁷ is selected from the group consisting of alkyl groups of from about 6 to 18 carbon atoms, and
R⁸ is selected from the group consisting of R² and —CH₂C₆H₅.

6. The method as claimed in claim 5 wherein the surfactant of (b) is selected from the group consisting of nonionic surfactants, sarcosine anionic, amphoteric surfactants and mixtures thereof.

7. The method as claimed in claim 6 wherein the surfactant is selected from nonionic surfactants selected from the group consisting of C₈ to C₁₈ alcohol ethoxylates containing from about 3 to 50 moles of ethylene oxide, C₈ to C₁₈ esters of sorbitan and polyethoxylated sorbitan, and C₈ to C₁₈ fatty acids containing from 3 to 50 moles of ethylene oxide, C₈ to C₁₈ alcohols, C₈ to C₁₈ diols, sodium lauroyl sarcosinate, sodium cocoyl sarcosinate, and amphoteric surfactants selected from the group consisting of C₈ to C₁₈ betaines and C₈ to C₁₈ amidoalkyl betaines.

8. The method as claimed in claim 3 wherein x is 0, A is —OCH₃, D is selected from the group consisting of methyl, and —R³N(+)R²R⁴R⁵X(−) there X is chloride, R³ is propylene, and (i) R² and R⁴ are each methyl and R⁵ is octadecyl, (ii) R² is methyl and R⁴ and R⁵ are each decyl or (iii) R², R⁴ and R⁵ are each methyl.

9. The method as claimed in claim 8 wherein the water soluble organic quaternary ammonium compound is selected from the group consisting of R⁷R⁸N(+)(R²)₂X(−) and C₅H₅N(+)R⁷X(−) where R⁸ methyl or —CH₂C₆H₅, R² is methyl, X is chloride and the surfactant in step I (b) is selected from nonionic surfactants selected from the group consisting of C₈ to C₁₈ alcohol ethoxylates containing from about 3 to 50 moles of ethylene oxide, C₈ to C₁₈ fatty acid esters of sorbitan and polyoxyethylated sorbitan, C₈ to C₁₈ fatty acid esters and amides containing from about 2 to 50 moles of ethylene oxide, C₈ to C₁₈ alcohols, C₈ to C₁₈ diols, block copolymers of polyethyleneoxide and polypropylene oxide, ethoxylated and propoxylated C₈ to C₁₈ fatty alcohols, C₈ to C₁₈ alkyl amine oxides, C₈ to C₁₈ fatty amindoamine, C₈ to C₁₈ fatty alkanolamides, and C₈ to C₁₈ fatty acid esters of glycerine, sarcosine anionic surfactants selected from the group consisting of sodium lauroyl sarcosinate and sodium cocoyl sarcosinate, and amphoteric surfactants selected from the group consisting of C₈ to C₁₈ alkyl betaines and C₈ to C₁₈ amidoalkyl betaines, the pH is from 3 to 13.

10. The method as claimed in claim 9 therein the amount of water soluble organosilane is from about 0.0.1% to 2%, the amount of soluble organic quaternary ammonium compound is from about 0.1% to 5% and the total amount of nonionic, sarcosine anionic, and amphoteric surfactant is from about 1% to 5%.

11. The method as claimed in claim 9 wherein the water soluble organic quatenary ammonium compound is benzalkonium chloride.

12. The method as claimed in claim 1 wherein x is 0 and A is —OR¹ where R¹ is R² or hydrogen and R² is an alkyl group of 1 to 4 carbon atoms.

13. The method as claimed in claim 2 wherein x is 0 and A is —OR¹ where R¹ is R² or hydrogen and R² is an alkyl group of 1 to 4 carbon atoms.

14. A method of improving the storage stability and broadening the pH stability of an aqueous solution containing from about 0.001% to 5% by weight of a water soluble organosizane of the formula

provided that the organosizane forms a clear solution in water at 25° C. at the intended level of use, which method comprises
I. including within the solution
  a. from about 0.05% to 10% by weight of the total aqueous solution of a water soluble organic quaternary ammonium compound which is free of silicon atoms and contains at least one nitrogen-bonded hydrocarbon group of at least 8 carbons and
  b. from about 0.5% to 30% by weight of the total aqueous solution of at least one surfactant selected from the group consisting of nonionic, amphoteric, sarcosine anionic, and cationic surfactants other than the compounds of (a); wherein the amounts of (a) and (b) present are effective to improve the storage stability of and to broaden the pH stability of the resulting solution; and
II. including within the solution a sufficient amount of an acid or a base to obtain a solution pH of from about 1 to about 13.5,
wherein each
A is —OH or a hydrolyzable group,
B is an alkyl group of from 1 to 4 carbon atoms,
x has a value of 0, 1 or 2, and
D is a hydrocarbon group of from 1 to 4 carbon atoms, phenyl, or a nonionic or cationic, substituted-hydrocarbon group containing at least one oxygen or nitrogen group or salts of such substituted-hydrocarbon groups.

15. The method as claimed in claim 14 wherein I(a) is a water soluble organic quaternary ammonium salt.

16. The method as claimed in claim 15 wherein A is selected from the group consisting of —OR¹ and —OR²⁴OR¹ where each R¹ is R² or hydrogen, R² is an alkyl group of 1 to 4 carbon atoms, R²⁴ is a divalent saturated hydrocarbon group of from 1 to 4 carbon atoms and x has a value of 0 or 1.

17. The method as claimed in claim 16 wherein D is selected from the group consisting of alkyl groups of from 1 to 4 carbon atoms, vinyl, allyl, glycidoxypropyl, —R³N(R⁴)ᵧH₂₋ᵧ, —R³N(+)(R⁴)ᵧH₃₋ᵧX(−), —R³NHR³N(R⁴)ᵧH₂₋ᵧ, —R³NHR³N(+)(R⁴)ᵧH₃₋ᵧX(−), —R³N(+)R²R⁴R⁵X(−) and

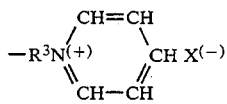

wherein
R[3] is a divalent saturated hydrocarbon group of from 1 to 12 carbon atoms; R[4] and R[5] are each selected from the group consisting of alkyl groups of 1 to 18 carbon atoms, —CH$_2$C$_6$H$_5$, —CH$_2$CH$_2$OH and —CH$_2$OH;
y has a value of 0, 1 or 2; and
X is an anion.

18. The method as claimed in claim 17 wherein the water soluble organic quaternary ammonium compound is selected from the group consisting of R[7]R[8]N(+)(R[2])$_2$X(−) and C$_5$H$_5$N(+)R[7]X(−) wherein
R[7] is selected from the group consisting of alkyl groups of from about 6 to 18 carbon atoms, and
R[8] is selected from the group consisting of R[2] and —CH$_2$C$_6$H$_5$.

19. The method as claimed in claim 18 wherein the surfactant of (b) is selected from the group consisting of nonionic surfactants, sarcosine anionic, amphoteric surfactants and mixtures thereof.

20. The method as claimed in claim 19 wherein the surfactant is selected from nonionic surfactants selected from the group consisting of C$_8$ to C$_{18}$ alcohol ethoxylates containing from about 3 to 50 moles of ethylene oxide, C$_8$ to C$_{18}$ esters of sorbitan and polyethoxylated sorbitan, and C$_8$ to C$_{18}$ fatty acids containing from 3 to 50 moles of ethylene oxide, C$_8$ to C$_{18}$ alcohols, C$_8$ to C$_{18}$ diols, sodium lauroyl sarcosinate, sodium cocoyl sarcosinate, and amphoteric surfactants selected from the group consisting of C$_8$ to C$_{18}$ betaines and C$_8$ to C$_{18}$ amidoalkyl betaines.

21. The method as claimed in claim 16 wherein x is 0, A is —OCH$_3$, D is selected from the group consisting of methyl, and —R[3]N(+)R[2]R[4]R[5]X(−) where X is chloride, R[3] is propylene, and (i) R[2] and R[4] are each methyl and R[5] is octadecyl, (ii) R[2] is methyl and R[4] and R[5] are each decyl or (iii) R[2], R[4] and R[5] are each methyl.

22. The method as claimed in claim 21 wherein the water soluble organic quaternary ammonium compound is selected from the group consisting of R[7]R[8]N(+)(R[2])$_2$X(−) and C$_5$H$_5$N(+)R[7]X(−) where R[8] is methyl or —CH$_2$C$_6$H$_5$, R[2] is methyl, X is chloride and the surfactant in step I (b) is selected from nonionic surfactants selected from the group consisting of C$_8$ to C$_{18}$ alcohol ethoxylates containing from about 3 to 50 moles of ethylene oxide, C$_8$ to C$_{18}$ fatty acid esters of sorbitan and polyoxyethylated sorbitan, C$_8$ to C$_{18}$ fatty acid esters and amides containing from about 2 to 50 moles of ethylene oxide, C$_8$ to C$_{18}$ alcohols, C$_8$ to C$_{18}$ diols, block copolymers of polyethyleneoxide and polypropylene oxide, ethoxylated and propoxylated C$_8$ to C$_{18}$ fatty alcohols, C$_8$ to C$_{18}$ alkyl amine oxides, C$_8$ to C$_{18}$ fatty amindoamines, C$_8$ to C$_{18}$ fatty alkanolamides, and C$_8$ to C$_{18}$ fatty acid esters of glycerine, sarcosine anionic surfactants selected from the group consisting of sodium lauroyl sarcosinate and sodium cocoyl sarcosinate, and amphoteric surfactants selected from the group consisting of C$_8$ to C$_{18}$ alkyl betaines and C$_8$ to C$_{18}$ amidoalkyl betaines, the pH is from 3 to 13.

23. The method as claimed in claim 22 wherein the amount of water soluble organosilane is from about 0.01% to 2%, the amount of water soluble organic quaternary ammonium compound is from about 0.1% to 5% and the total amount of nonionic, sarcosine anionic, and amphoteric surfactant is from about 1% to 5%.

24. The method as claimed in claim 22 wherein the water soluble organic quaternary ammonium compound is benzalkonium chloride.

25. The method as claimed in claim 14 wherein x is 0 and A is —OR[1] where R[1] is R[2] or hydrogen and R[2] is an alkyl group of 1 to 4 carbon atoms.

26. The method as claimed in claim 15 wherein x is 0 and A is —OR[1] where R[1] is R[2] or hydrogen and R[2] is an alkyl group of 1 to 4 carbon atoms.

27. The aqueous solution obtained by the method of claim 1 wherein the surfactant in step I(b) is only selected from the group consisting of nonionic surfactants, sarcosine anionic, amphoteric surfactants and mixtures thereof.

28. The aqueous solution obtained by the method of claim 2 wherein the surfactant in step I(b) is selected only from the group consisting of nonionic surfactants, sarcosine anionic, amphoteric surfactants and mixtures thereof.

29. The aqueous solution obtained by the method of claim 3 wherein the surfactant in step I(b) is selected from the group consisting of nonionic surfactants, sarcosine anionic, amphoteric surfactants and mixtures thereof.

30. The aqueous solution obtained by the method of claim 4 wherein the surfactant in step I(b) is selected from the group consisting of nonionic surfactants, sarcosine anionic, amphoteric surfactants and mixtures thereof.

31. The aqueous solution obtained by the method of claim 5 wherein the surfactant in step I(b) is selected from the group consisting of nonionic surfactants, sarcosine anionic, amphoteric surfactants and mixtures thereof.

32. The aqueous solution obtained by the method of claim 6.

33. The aqueous solution obtained by the method of claim 7.

34. The aqueous solution obtained by the method of claim 8 wherein the surfactant in step I(b) is only selected from the group consisting of nonionic surfactants, sarcosine anionic, amphoteric surfactants and mixtures thereof.

35. The aqueous solution obtained by the method of claim 9.

36. The aqueous solution obtained by the method of claim 10.

37. The aqueous solution obtained by the method of claim 11 wherein the surfactant in step I(b) is only selected from the group consisting of nonionic surfactants, sarcosine anionic, amphoteric surfactants and mixtures thereof.

38. The aqueous solution obtained by the method of claim 12 wherein the surfactant in step I(b) is only selected from the group consisting of nonionic surfactants, sarcosine anionic, amphoteric surfactants and mixtures thereof.

39. The aqueous solution obtained by the method of claim 13 wherein the surfactant in step I(b) is only selected from the group consisting of nonionic surfactants, sarcosine anionic, amphoteric surfactants and mixtures thereof.

40. The aqueous solution obtained by the method of claim 14 wherein the surfactant in step I(b) is selected only from the group consisting of nonionic surfactants, sarcosine anionic, amphoteric surfactants and mixtures thereof.

41. The aqueous solution obtained by the method of claim 15 wherein the surfactant in step I(b) is selected from the group consisting of nonionic surfactants, sarcosine anionic, amphoteric surfactants and mixtures thereof.

42. The aqueous solution obtained by the method of claim 16 wherein the surfactant in step I(b) is selected from the group consisting of nonionic surfactants, sarcosine anionic, amphoteric surfactants and mixtures thereof.

43. The aqueous solution obtained by the method of claim 17 wherein the surfactant in step I(b) is selected from the group consisting of nonionic surfactants, sarcosine anionic, amphoteric surfactants and mixtures thereof.

44. The aqueous solution obtained by the method of claim 18 wherein the surfactant in step I(b) is only selected from the group consisting of nonionic surfactants, sarcosine anionic, amphoteric surfactants and mixtures thereof.

45. The aqueous solution obtained by the method of claim 19.

46. The aqueous solution obtained by the method of claim 20.

47. The aqueous solution obtained by the method of claim 21 wherein the surfactant in step I(b) is only selected only from the group consisting of nonionic surfactants, sarcosine anionic, amphoteric surfactants and mixtures thereof.

48. The aqueous solution obtained by the method of claim 22.

49. The aqueous solution obtained by the method of claim 23.

50. The aqueous solution obtained by the method of claim 24 wherein the surfactant in step I(b) is selected only from the group consisting of nonionic surfactants, sarcosine anionic, amphoteric surfactants and mixtures thereof.

51. The aqueous solution obtained by the method of claim 25 wherein the surfactant in step I(b) is selected only from the group consisting of nonionic surfactants, sarcosine anionic, amphoteric surfactants and mixtures thereof.

52. The aqueous solution obtained by the method of claim 26 wherein the surfactant in step I(b) is selected only from the group consisting of nonionic surfactants, sarcosine anionic, amphoteric surfactants and mixtures thereof.

* * * * *